US007229756B1

(12) United States Patent
Small et al.

(10) Patent No.: US 7,229,756 B1
(45) Date of Patent: Jun. 12, 2007

(54) ALPHA-2B-ADRENERGIC RECEPTOR POLYMORPHISMS

(75) Inventors: Kersten M. Small, Cincinnati, OH (US); Stephen B. Liggett, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 267 days.

(21) Appl. No.: 09/692,077

(22) Filed: Oct. 19, 2000

(51) Int. Cl.
*C12Q 1/68* (2006.01)
*C12P 19/34* (2006.01)

(52) U.S. Cl. .......................................... 435/6; 435/91.2

(58) Field of Classification Search .................... 435/6, 435/19, 91.2, 91.5, 91.52; 536/23.5, 24.31, 536/24.33, 25.32; 530/350
See application file for complete search history.

(56) References Cited

U.S. PATENT DOCUMENTS

| | | | | |
|---|---|---|---|---|
| 5,595,880 | A | 1/1997 | Weinshank et al. | 435/7.21 |
| 5,648,482 | A | 7/1997 | Meyer | 536/24.33 |
| 5,846,710 | A | 12/1998 | Bajaj | 435/6 |
| 5,856,092 | A | 1/1999 | Dale et al. | 435/6 |
| 5,888,819 | A | 3/1999 | Goelet et al. | 435/5 |
| 5,981,174 | A | 11/1999 | Wolf et al. | 435/6 |
| 6,004,744 | A | 12/1999 | Goelet et al. | 435/5 |
| 6,013,431 | A | 1/2000 | Soderlund et al. | 435/5 |
| 6,156,503 | A | 12/2000 | Drazen et al. | 435/6 |
| 6,566,101 | B1 * | 5/2003 | Shuber et al. | 435/91.2 |
| 2001/0016338 | A1 * | 8/2001 | Snapir et al. | 435/69.1 |

FOREIGN PATENT DOCUMENTS

| | | |
|---|---|---|
| WO | WO 0129082 | 4/2001 |

OTHER PUBLICATIONS

Newton, C.R. Chapter 6: Primers, in PCR Essential Data, C.R. Newton, ed., John Wiley & Sons, Chichester, 1995, pp. 49-56.*

Ho et al. (American Journal of Medical Genetics, vol. 81, No. 6, p. 510, Abstract #93).*

Salonen et al. (Circulation, Oct. 2000, vol. 102, No. 18, Supplement, p. 859, abstract #4125).*

Pollin et al. Obesity Research, Oct. 2000, vol. 8, Supplement 1p. 113S, abstract PE4.*

Limbird, L. E. (1988) FASEB J 2, 2686-2695.

Eason, M. G. and Liggett, S. B. (1993) Mol.Pharmacol. 44, 70-75.

Handy, D. E., Flordellis, C. S., Bogdanova, N. N., Bresnahan, M. R., and Gavras, H. (1993) Hypertension 21, 861-865.

Tavares, A., Handy, D. E., Bogdanova, N. N., Rosene, D. L., and Gavras, H. (1996) Hypertension 27, 449-455.

Hein, L., Limbird, L. E., Eglen, R. M., and Kobilka, B. K. (1999) Ann NY Acad Sci 881, 265-271.

Rohrer, D. K. and Kobilka, B. K. (1998) Physiol Rev 78, 35-52.

Ruffolo, R. R., Jr., Nichols, A. J., Stadel, J. M., and Hieble, J. P. (1993) Annu Rev Pharmacol Toxicol 32, 243-279.

Sallinen, J., Haapalinna, A., Viitamaa, T., Kobilka, B. K., and Scheinin, M. (1998) The Journal of Neuroscience 18, 3035-3042.

Sallinen, J., Haapalinna, A., Macdonald, E., Viitamaa, T., Lahdesmaki, J., Rybnikova, E., Pelto-Huikko, M., Kobilka, B. K., and Scheinin, M. (1999) Mol Psychiatry 4, 443-452.

Altman, J. D., Trendelenburg, A. U., MacMillan, L., Bernstein, D., Limbird, L., Starke, K., Kobilka, B. K., and Hein, L. (1999) Mol.Pharmacol. 56, 154-161.

Hein, L., Altman, J. D., and Kobilka, B. K. (1999) Nature 402, 181-184.

Link, R. E., Desai, K., Hein, L., Stevens, M. E., Chruscinski, A., Bernstein, D., Barsh, G. S., and Kobilka, B. K. (1996) Science 273, 803-805.

Makaritsis, K. P., Handy, D. E., Johns, C., Kobilka, B., Gavras, I., and Gavras, H. (1999) Hypertension 33, 14-17.

Liggett, S. B., Ostrowski, J., Chestnut, L. C., Kurose, H., Raymond, J. R., Caron, M. G., and Lefkowitz, R. J. (1992) J.Biol.Chem. 267, 4740-4746.

Eason, M. G., Moreira, S. P., and Liggett, S. B. (1995) J.Biol.Chem. 270, 4681-4688.

Eason, M. G. and Liggett, S. B. (1992) J.Biol.Chem. 267, 25473-25479.

Jewell-Motz, E. A. and Liggett, S. B. (1995) Biochem 34, 11946-11953.

Kurose, H. and Lefkowitz, R. J. (1994) J.Biol.Chem. 269, 10093-10099.

Pitcher, J. A., Freedman, N. J., and Lefkowitz, R. J. (1998) Annu Rev Biochem 67, 692.

Heinonen, P., Koulu, M., Pesonen, U., Karvonen, M. K., Rissanen, A., Laakso, M., Valve, R., Uusitupa, M., and Scheinin, M. (1999) J Clin Endocrinol Metab 84, 2429-2433.

Baldwin, C. T., Schwartz, F., Baima, J., Burzstyn, M., DeStefano, A. L., Gavras, I., Handy, D. E., Joost, O., Martel, T., Manolis, A., Nicolaou, M., Bresnahan, M., Farrer, L., and Gavras, H. (1999) Am J Hypertens 12, 853-857.

Eason, M. G., Jacinto, M. T., and Liggett, S. B. (1994) Mol. Pharmacol. 45, 696-702.

Jewell-Motz, E. A., Small, K. M., and Liggett, S. B. (2000) J.Biol.Chem.

Small, K. M., Forbes, S. L., Rahman, F. F., Bridges, K. M., and Liggett, S. B. (2000) J.Biol.Chem. 275, 23059-23064.

Hausdorff, W. P., Bouvier, M., O'Dowd, B. F., Irons, G. P., Caron, M. G., and Lefkowitz, R. J. (1989) J.Biol.Chem. 264, 12657-12665.

Baron, B. M. and Siegel, B. W. (1990) Mol Pharmacol 38, 348-356.

Smith, P. K., Krohn, R. I., Hermanson, G. T., Mallia, A. K., Gartner, F. H., Provenzano, M. D., Fujimoto, E. K., Goeke, N. M., Olson, B. J., and Klenk, D. C. (1985) Anal.Biochem. 150, 76-85.

(Continued)

*Primary Examiner*—Juliet C. Switzer
(74) *Attorney, Agent, or Firm*—Fenwick & West LLP

(57) ABSTRACT

The present invention includes polymorphisms in nucleic acids encoding the alpha-2B adrenergic receptor and expressed alpha-2B adrenergic receptor molecule. The invention also pertains to methods and molecules for detecting such polymorphisms. The invention further pertains to the use of such molecules and methods in the diagnosis, prognosis, and treatment of diseases such as cardiovascular and central nervous system diseases.

11 Claims, 4 Drawing Sheets

OTHER PUBLICATIONS

Onorato, J. J., Palczewski, K., Regan, J. W., Caron, M. G., Lefkowitz, R. J., and Benovic, J. L. (1991) Biochem 30, 5118-5125.

Jewell-Motz, E. A. and Liggett, S. B. (1996) J.Biol.Chem. 271, 18082-18087.

MacMillan, L. B., Hein, L., Smith, M. S., Piascik, M. T., and Limbird, L. E. (1996) Science 273, 801-805.

Munroe, P. B. and Caulfield, M. J. (2000) Curr Opin Genet Dev 10, 325-329.

"Introduction to α-adrenoceptors," http://www.adrenoceptor.com/alphaintro.htm (Website visited Apr. 2, 2001), (author, vol., pp.-N/A).

Robinson, E. & Hudson, A. "Adrenoceptor Pharmacology," http://www.tocris.com/adrenoceptor.htm, Nov. 1998 (Website visited Mar. 19, 2001), (vol., pp.-N/A).

Heinonen P. et al: "Identification of a three-amino acid deletion in the alpha2B-adrenergic receptor that is associated with reduced basal metabolic rate in obese subjects." *The Journal of Clinical Endocrinology and Metabolism*, United States, Jul. 1999, vol. 84, No. 7, pp. 2429-2433.

Baldwin C.T., et al: "Identification of a polymorphic glutamic acid stretch in the alpha2B-adrenergic receptor and lack of linkage with essential hypertension." *American Journal of Hypertension: Journal of the American Society of Hypertension*, United States, Sep. 1999, vol. 12, No. 9, Pt. 1, pp. 853-857.

Jewell-Motz, E.A. et al: "An acidic motif within the third intracellular loop of the alpha2C2 adrenergic receptor is required for agonist-promoted phosphorylation and desensitization." *Biochemistry*, United States Sep. 19, 1995, vol. 34, No. 37, Sep. 19, 1995, pp. 11946-11953.

Comings, D.E., et al: "Additive effect of three noradrenergic genes (ADRA2a, ADRA2C, DBH) on attention-deficit hyperactivity disorder and learning disabilities in Tourette syndrome subjects." *Clinical Genetics*, Denmark, Mar. 1999, vol. 55, No. 3, pp. 160-172.

Makaritsis K.P., et al: "Role of the alpha2B-adrenergic receptor in the development of salt-induced hypertension." *Hypertension*. United States, Jan. 1999, vol. 33, No. 1, Jan. 1999, pp. 14-17.

Michel M.C., et al: "Functional correlates of alpha(2A)-adrenoceptor gene polymorphism in the HANE study." *Nephrology, Dialysis. Transplantation: Official Publication of the European Dialysis and Transplant Association-European Renal Association*. England, Nov. 1999, vol. 14, No. 11, pp. 2657-2663.

Freeman K., et al: "Genetic polymorphism of the alpha 2-adrenergic receptor is associated with increased platelet aggregation, baroreceptor sensitivity, and salt excretion in normotensive humans." *American Journal of Hypertension: Journal of the American Society of Hypertension*. United States, Sep. 1995, vol. 8, No. 9, pp. 863-869.

Small K.M., et al: "Polymorphic deletion of three intracellular acidic residues of the alpha 2B-adrenergic receptor decreases G protein-coupled receptor kinase-mediated phosphorylation and desensitization." *The Journal of Biological Chemistry*. United States, Feb. 16, 2001, vol. 276, No. 7, pp. 4917-4922.

Snapir A., et al: "An insertion/deletion polymorphism in the alpha2B-adrenergic receptor gene is a novel genetic risk factor for acute coronary events." *Journal of the American College of Cardiology*. United States, May 2001, vol. 37, No. 6, pp. 1516-1522.

* cited by examiner

SEQUENCE LISTING

```
<160> NUMBER OF SEQ ID NOS: 26

<210> SEQ ID NO 1
<211> LENGTH: 1353
<212> TYPE: DNA
<213> ORGANISM: Homo sapiens

<400> SEQUENCE: 1

atggaccacc aggaccccta ctccgtgcag gccacagcgg ccatagcggc ggccatcacc      60

ttcctcattc tctttaccat cttcggcaac gctctggtca tcctggctgt gttgaccagc     120

cgctcgctgc gcgcccctca gaacctgttc ctggtgtcgc tggccgccgc cgacatcctg     180
```

-continued

```
gtggccacgc tcatcatccc tttctcgctg gccaacgagc tgctgggcta ctggtacttc    240
cggcgcacgt ggtgcgaggt gtacctggcg ctcgacgtgc tcttctgcac ctcgtccatc    300
gtgcacctgt gcgccatcag cctggaccgc tactgggccg tgagccgcgc gctggagtac    360
aactccaagc gcaccccgcg ccgcatcaag tgcatcatcc tcactgtgtg gctcatcgcc    420
gccgtcatct cgctgccgcc cctcatctac aagggcgacc agggccccca gccgcgcggg    480
cgcccccagt gcaagctcaa ccaggaggcc tggtacatcc tggcctccag catcggatct    540
ttctttgctc cttgcctcat catgatcctt gtctacctgc gcatctacct gatcgccaaa    600
cgcagcaacc gcagaggtcc cagggccaag gggggcctgg ggcagggtga gtccaagcag    660
ccccgacccg accatggtgg ggctttggcc tcagccaaac tgccagccct ggcctctgtg    720
gcttctgcca gagaggtcaa cggacactcg aagtccactg gggagaagga ggagggggag    780
acccctgaag atactgggac ccgggccttg ccacccagtt gggctgccct tcccaactca    840
ggccagggcc agaaggaggg tgtttgtggg gcatctccag aggatgaagc tgaagaggag    900
gaagaggagg aggaggagga ggaagagtgt gaaccccagg cagtgccagt gtctccggcc    960
tcagcttgca gccccccgct gcagcagcca cagggctccc gggtgctggc caccctacgt   1020
ggccaggtgc tcctgggcag gggcgtgggt gctataggtg ggcagtggtg gcgtcgaagg   1080
gcgcagctga cccgggagaa gcgcttcacc ttcgtgctgg ctgtggtcat tggcgttttt   1140
gtgctctgct ggttcccctt cttcttcagc tacagcctgg gcgccatctg cccgaagcac   1200
tgcaaggtgc cccatggcct cttccagttc ttcttctgga tcggctactg caacagctca   1260
ctgaaccctg ttatctacac catcttcaac caggacttcc gccgtgcctt ccggaggatc   1320
ctgtgccgcc cgtggaccca gacggcctgg tga                                1353
```

<210> SEQ ID NO 2
<211> LENGTH: 1344
<212> TYPE: DNA
<213> ORGANISM: Homo sapiens

<400> SEQUENCE: 2

```
atggaccacc aggacccccta ctccgtgcag gccacagcgg ccatagcggc ggccatcacc     60
ttcctcattc tctttaccat cttcggcaac gctctggtca tcctggctgt gttgaccagc    120
cgctcgctgc gcgcccctca gaacctgttc ctggtgtcgc tggccgccgc cgacatcctg    180
gtggccacgc tcatcatccc tttctcgctg gccaacgagc tgctgggcta ctggtacttc    240
cggcgcacgt ggtgcgaggt gtacctggcg ctcgacgtgc tcttctgcac ctcgtccatc    300
gtgcacctgt gcgccatcag cctggaccgc tactgggccg tgagccgcgc gctggagtac    360
aactccaagc gcaccccgcg ccgcatcaag tgcatcatcc tcactgtgtg gctcatcgcc    420
gccgtcatct cgctgccgcc cctcatctac aagggcgacc agggccccca gccgcgcggg    480
cgcccccagt gcaagctcaa ccaggaggcc tggtacatcc tggcctccag catcggatct    540
ttctttgctc cttgcctcat catgatcctt gtctacctgc gcatctacct gatcgccaaa    600
cgcagcaacc gcagaggtcc cagggccaag gggggcctgg ggcagggtga gtccaagcag    660
ccccgacccg accatggtgg ggctttggcc tcagccaaac tgccagccct ggcctctgtg    720
gcttctgcca gagaggtcaa cggacactcg aagtccactg gggagaagga ggagggggag    780
acccctgaag atactgggac ccgggccttg ccacccagtt gggctgccct tcccaactca    840
ggccagggcc agaaggaggg tgtttgtggg gcatctccag aggatgaagc tgaagaggag    900
```

-continued

```
gaggaggagg aggaagagtg tgaaccccag gcagtgccag tgtctccggc ctcagcttgc    960

agccccccgc tgcagcagcc acagggctcc cgggtgctgg ccaccctacg tggccaggtg   1020

ctcctgggca ggggcgtggg tgctataggt gggcagtggt ggcgtcgaag ggcgcagctg   1080

acccgggaga agcgcttcac cttcgtgctg gctgtggtca ttggcgtttt tgtgctctgc   1140

tggttcccct tcttcttcag ctacagcctg ggcgccatct gcccgaagca ctgcaaggtg   1200

ccccatggcc tcttccagtt cttcttctgg atcggctact gcaacagctc actgaaccct   1260

gttatctaca ccatcttcaa ccaggacttc cgccgtgcct tccggaggat cctgtgccgc   1320

ccgtggaccc agacggcctg gtga                                          1344


<210> SEQ ID NO 3
<211> LENGTH: 9
<212> TYPE: DNA
<213> ORGANISM: Homo sapiens

<400> SEQUENCE: 3

gaagaggag                                                              9


<210> SEQ ID NO 4
<211> LENGTH: 9
<212> TYPE: DNA
<213> ORGANISM: Homo sapiens

<400> SEQUENCE: 4

gaggaggag                                                              9


<210> SEQ ID NO 5
<211> LENGTH: 9
<212> TYPE: DNA
<213> ORGANISM: Homo sapiens

<400> SEQUENCE: 5

ctcctcttc                                                              9


<210> SEQ ID NO 6
<211> LENGTH: 9
<212> TYPE: DNA
<213> ORGANISM: Homo sapiens

<400> SEQUENCE: 6

ctcctcctc                                                              9


<210> SEQ ID NO 7
<211> LENGTH: 450
<212> TYPE: PRT
<213> ORGANISM: Homo sapiens

<400> SEQUENCE: 7

Met Asp His Gln Asp Pro Tyr Ser Val Gln Ala Thr Ala Ala Ile Ala
1               5                   10                  15

Ala Ala Ile Thr Phe Leu Ile Leu Phe Thr Ile Phe Gly Asn Ala Leu
            20                  25                  30

Val Ile Leu Ala Val Leu Thr Ser Arg Ser Leu Arg Ala Pro Gln Asn
        35                  40                  45

Leu Phe Leu Val Ser Leu Ala Ala Ala Asp Ile Leu Val Ala Thr Leu
    50                  55                  60

Ile Ile Pro Phe Ser Leu Ala Asn Glu Leu Leu Gly Tyr Trp Tyr Phe
65                  70                  75                  80
```

-continued

```
Arg Arg Thr Trp Cys Glu Val Tyr Leu Ala Leu Asp Val Leu Phe Cys
                85                  90                  95

Thr Ser Ser Ile Val His Leu Cys Ala Ile Ser Leu Asp Arg Tyr Trp
            100                 105                 110

Ala Val Ser Arg Ala Leu Glu Tyr Asn Ser Lys Arg Thr Pro Arg Arg
        115                 120                 125

Ile Lys Cys Ile Ile Leu Thr Val Trp Leu Ile Ala Ala Val Ile Ser
    130                 135                 140

Leu Pro Pro Leu Ile Tyr Lys Gly Asp Gln Gly Pro Gln Pro Arg Gly
145                 150                 155                 160

Arg Pro Gln Cys Lys Leu Asn Gln Glu Ala Trp Tyr Ile Leu Ala Ser
                165                 170                 175

Ser Ile Gly Ser Phe Phe Ala Pro Cys Leu Ile Met Ile Leu Val Tyr
            180                 185                 190

Leu Arg Ile Tyr Leu Ile Ala Lys Arg Ser Asn Arg Arg Gly Pro Arg
        195                 200                 205

Ala Lys Gly Gly Pro Gly Gln Gly Glu Ser Lys Gln Pro Arg Pro Asp
    210                 215                 220

His Gly Gly Ala Leu Ala Ser Ala Lys Leu Pro Ala Leu Ala Ser Val
225                 230                 235                 240

Ala Ser Ala Arg Glu Val Asn Gly His Ser Lys Ser Thr Gly Glu Lys
                245                 250                 255

Glu Glu Gly Glu Thr Pro Glu Asp Thr Gly Thr Arg Ala Leu Pro Pro
            260                 265                 270

Ser Trp Ala Ala Leu Pro Asn Ser Gly Gln Gly Gln Lys Glu Gly Val
        275                 280                 285

Cys Gly Ala Ser Pro Glu Asp Glu Ala Glu Glu Glu Glu Glu Glu Glu
    290                 295                 300

Glu Glu Glu Glu Glu Cys Glu Pro Gln Ala Val Pro Val Ser Pro Ala
305                 310                 315                 320

Ser Ala Cys Ser Pro Pro Leu Gln Gln Pro Gln Gly Ser Arg Val Leu
                325                 330                 335

Ala Thr Leu Arg Gly Gln Val Leu Leu Gly Arg Gly Val Gly Ala Ile
            340                 345                 350

Gly Gly Gln Trp Trp Arg Arg Arg Ala Gln Leu Thr Arg Glu Lys Arg
        355                 360                 365

Phe Thr Phe Val Leu Ala Val Val Ile Gly Val Phe Val Leu Cys Trp
    370                 375                 380

Phe Pro Phe Phe Phe Ser Tyr Ser Leu Gly Ala Ile Cys Pro Lys His
385                 390                 395                 400

Cys Lys Val Pro His Gly Leu Phe Gln Phe Phe Phe Trp Ile Gly Tyr
                405                 410                 415

Cys Asn Ser Ser Leu Asn Pro Val Ile Tyr Thr Ile Phe Asn Gln Asp
            420                 425                 430

Phe Arg Arg Ala Phe Arg Arg Ile Leu Cys Arg Pro Trp Thr Gln Thr
        435                 440                 445

Ala Trp
    450
```

<210> SEQ ID NO 8
<211> LENGTH: 447
<212> TYPE: PRT
<213> ORGANISM: Homo sapiens

<400> SEQUENCE: 8

-continued

```
Met Asp His Gln Asp Pro Tyr Ser Val Gln Ala Thr Ala Ala Ile Ala
1               5                   10                  15

Ala Ala Ile Thr Phe Leu Ile Leu Phe Thr Ile Phe Gly Asn Ala Leu
            20                  25                  30

Val Ile Leu Ala Val Leu Thr Ser Arg Ser Leu Arg Ala Pro Gln Asn
        35                  40                  45

Leu Phe Leu Val Ser Leu Ala Ala Ala Asp Ile Leu Val Ala Thr Leu
    50                  55                  60

Ile Ile Pro Phe Ser Leu Ala Asn Glu Leu Leu Gly Tyr Trp Tyr Phe
65                  70                  75                  80

Arg Arg Thr Trp Cys Glu Val Tyr Leu Ala Leu Asp Val Leu Phe Cys
                85                  90                  95

Thr Ser Ser Ile Val His Leu Cys Ala Ile Ser Leu Asp Arg Tyr Trp
            100                 105                 110

Ala Val Ser Arg Ala Leu Glu Tyr Asn Ser Lys Arg Thr Pro Arg Arg
        115                 120                 125

Ile Lys Cys Ile Ile Leu Thr Val Trp Leu Ile Ala Ala Val Ile Ser
    130                 135                 140

Leu Pro Pro Leu Ile Tyr Lys Gly Asp Gln Gly Pro Gln Pro Arg Gly
145                 150                 155                 160

Arg Pro Gln Cys Lys Leu Asn Gln Glu Ala Trp Tyr Ile Leu Ala Ser
                165                 170                 175

Ser Ile Gly Ser Phe Phe Ala Pro Cys Leu Ile Met Ile Leu Val Tyr
            180                 185                 190

Leu Arg Ile Tyr Leu Ile Ala Lys Arg Ser Asn Arg Arg Gly Pro Arg
        195                 200                 205

Ala Lys Gly Gly Pro Gly Gln Gly Glu Ser Lys Gln Pro Arg Pro Asp
    210                 215                 220

His Gly Gly Ala Leu Ala Ser Ala Lys Leu Pro Ala Leu Ala Ser Val
225                 230                 235                 240

Ala Ser Ala Arg Glu Val Asn Gly His Ser Lys Ser Thr Gly Glu Lys
                245                 250                 255

Glu Glu Gly Glu Thr Pro Glu Asp Thr Gly Thr Arg Ala Leu Pro Pro
            260                 265                 270

Ser Trp Ala Ala Leu Pro Asn Ser Gly Gln Gly Gln Lys Glu Gly Val
        275                 280                 285

Cys Gly Ala Ser Pro Glu Asp Glu Ala Glu Glu Glu Glu Glu Glu Glu
    290                 295                 300

Glu Glu Cys Glu Pro Gln Ala Val Pro Val Ser Pro Ala Ser Ala Cys
305                 310                 315                 320

Ser Pro Pro Leu Gln Gln Pro Gln Gly Ser Arg Val Leu Ala Thr Leu
                325                 330                 335

Arg Gly Gln Val Leu Leu Gly Arg Gly Val Gly Ala Ile Gly Gly Gln
            340                 345                 350

Trp Trp Arg Arg Arg Ala Gln Leu Thr Arg Glu Lys Arg Phe Thr Phe
        355                 360                 365

Val Leu Ala Val Val Ile Gly Val Phe Val Leu Cys Trp Phe Pro Phe
    370                 375                 380

Phe Phe Ser Tyr Ser Leu Gly Ala Ile Cys Pro Lys His Cys Lys Val
385                 390                 395                 400

Pro His Gly Leu Phe Gln Phe Phe Phe Trp Ile Gly Tyr Cys Asn Ser
                405                 410                 415
```

-continued

```
Ser Leu Asn Pro Val Ile Tyr Thr Ile Phe Asn Gln Asp Phe Arg Arg
            420                 425                 430

Ala Phe Arg Arg Ile Leu Cys Arg Pro Trp Thr Gln Thr Ala Trp
        435                 440                 445


<210> SEQ ID NO 9
<211> LENGTH: 16
<212> TYPE: PRT
<213> ORGANISM: Homo sapiens

<400> SEQUENCE: 9

Glu Asp Glu Ala Glu Glu Glu Glu Glu Glu Glu Glu Glu Glu Glu Glu
1               5                   10                  15


<210> SEQ ID NO 10
<211> LENGTH: 13
<212> TYPE: PRT
<213> ORGANISM: Homo sapiens

<400> SEQUENCE: 10

Glu Asp Glu Ala Glu Glu Glu Glu Glu Glu Glu Glu Glu
1               5                   10


<210> SEQ ID NO 11
<211> LENGTH: 3
<212> TYPE: PRT
<213> ORGANISM: Homo sapiens

<400> SEQUENCE: 11

Glu Glu Glu
1


<210> SEQ ID NO 12
<211> LENGTH: 3
<212> TYPE: PRT
<213> ORGANISM: Homo sapiens

<400> SEQUENCE: 12

Cys Glu Pro
1


<210> SEQ ID NO 13
<211> LENGTH: 21
<212> TYPE: DNA
<213> ORGANISM: Homo sapiens

<400> SEQUENCE: 13

gctcatcatc cctttctcgc t                                            21


<210> SEQ ID NO 14
<211> LENGTH: 21
<212> TYPE: DNA
<213> ORGANISM: Homo sapiens

<400> SEQUENCE: 14

aaagccccac catggtcggg t                                            21


<210> SEQ ID NO 15
<211> LENGTH: 20
<212> TYPE: DNA
<213> ORGANISM: Homo sapiens

<400> SEQUENCE: 15

ctgatcgcca aacgagcaac                                              20
```

<210> SEQ ID NO 16
<211> LENGTH: 20
<212> TYPE: DNA
<213> ORGANISM: Homo sapiens

<400> SEQUENCE: 16
aaaaacgcca atgaccacag 20

<210> SEQ ID NO 17
<211> LENGTH: 18
<212> TYPE: DNA
<213> ORGANISM: Homo sapiens

<400> SEQUENCE: 17
tgtaaaacga cggccagt 18

<210> SEQ ID NO 18
<211> LENGTH: 18
<212> TYPE: DNA
<213> ORGANISM: Homo sapiens

<400> SEQUENCE: 18
caggaaacag ctatgacc 18

<210> SEQ ID NO 19
<211> LENGTH: 21
<212> TYPE: DNA
<213> ORGANISM: Homo sapiens

<400> SEQUENCE: 19
agaaggaggg tgtttgtggg g 21

<210> SEQ ID NO 20
<211> LENGTH: 21
<212> TYPE: DNA
<213> ORGANISM: Homo sapiens

<400> SEQUENCE: 20
acctatagca cccacgcccc t 21

<210> SEQ ID NO 21
<211> LENGTH: 21
<212> TYPE: DNA
<213> ORGANISM: Homo sapiens

<400> SEQUENCE: 21
ggccgacgct cttgtctagc c 21

<210> SEQ ID NO 22
<211> LENGTH: 20
<212> TYPE: DNA
<213> ORGANISM: Homo sapiens

<400> SEQUENCE: 22
caaggggttc ctaagatgag 20

<210> SEQ ID NO 23
<211> LENGTH: 9
<212> TYPE: PRT
<213> ORGANISM: Homo sapiens

<400> SEQUENCE: 23

-continued

```
Tyr Pro Tyr Asp Val Pro Asp Tyr Ala
1               5


<210> SEQ ID NO 24
<211> LENGTH: 69
<212> TYPE: DNA
<213> ORGANISM: Homo sapiens

<400> SEQUENCE: 24

gggcatctcc agaggatgaa gctgaagagg aggaagagga ggaggaggag gaggaagagt     60

gtgaacccc                                                             69


<210> SEQ ID NO 25
<211> LENGTH: 60
<212> TYPE: DNA
<213> ORGANISM: Homo sapiens

<400> SEQUENCE: 25

gggcatctcc agaggatgaa gctgaagagg aggaggagga ggaggaagag tgtgaacccc     60


<210> SEQ ID NO 26
<211> LENGTH: 233
<212> TYPE: PRT
<213> ORGANISM: Homo sapiens

<400> SEQUENCE: 26

Asn Gln Glu Ala Trp Tyr Ile Leu Ala Ser Ser Ile Gly Ser Phe Phe
1               5                   10                  15

Ala Pro Cys Ala Ile Met Ile Leu Val Tyr Leu Arg Ile Tyr Leu Ile
            20                  25                  30

Ala Lys Arg Ser Asn Arg Arg Gly Pro Arg Ala Lys Gly Gly Pro Gly
        35                  40                  45

Gln Gly Glu Ser Lys Gln Pro Arg Pro Asp His Gly Gly Ala Leu Ala
    50                  55                  60

Ser Ala Lys Leu Pro Ala Leu Ala Ser Val Ala Ser Ala Arg Glu Val
65                  70                  75                  80

Asn Gly His Ser Lys Ser Thr Gly Glu Lys Glu Glu Gly Glu Thr Pro
                85                  90                  95

Glu Asp Thr Gly Thr Arg Ala Leu Pro Pro Ser Trp Ala Ala Leu Pro
            100                 105                 110

Asn Ser Gly Gln Gly Gln Lys Glu Gly Val Cys Gly Ala Ser Pro Glu
        115                 120                 125

Asp Glu Ala Glu Glu Glu Glu Glu Glu Glu Glu Glu Glu Glu Glu Cys
    130                 135                 140

Glu Pro Gln Ala Val Pro Val Ser Pro Ala Ser Ala Cys Ser Pro Pro
145                 150                 155                 160

Leu Gln Gln Pro Gln Gly Ser Arg Val Leu Ala Thr Leu Arg Gly Gln
                165                 170                 175

Val Leu Leu Gly Arg Gly Val Gly Ala Ile Gly Gly Gln Trp Trp Arg
            180                 185                 190

Arg Arg Ala Gln Leu Thr Arg Glu Lys Arg Phe Thr Phe Val Leu Ala
        195                 200                 205

Val Val Ile Gly Val Phe Val Leu Cys Trp Phe Pro Phe Phe Phe Ser
    210                 215                 220

Tyr Ser Leu Gly Ala Ile Cys Pro Lys
225                 230
```

ALPHA-2B-ADRENERGIC RECEPTOR POLYMORPHISMS

This invention was made, in part, with government support by National Institutes of Health grants ES06096, and HL53436. The U.S. Government may have certain rights in this invention.

Throughout this application, various references are referred to. Disclosures of these publications in their entireties are hereby incorporated by reference into this application to describe more fully the state of the art to which this invention pertains.

FIELD OF THE INVENTION

The invention relates to a polymorphism in the gene encoding an alpha adrenergic receptor subtype. Such a polymorphism results in altered alpha-adrenergic receptor function and can cause or modify a disease and/or alter the response to pharmacologic treatment. More specifically, the present invention relates to specific polymorphisms in the alpha-2B adrenergic receptor gene and polymorphisms in the expressed alpha-2B adrenergic receptor. The invention further relates to methods and molecules for identifying one or more polymorphisms in the alpha-2B adrenergic receptor gene and alpha-2B adrenergic receptor, methods of diagnosing, prognosing and treating individuals with diseases associated with one or more polymorphisms in the alpha-2B adrenergic receptor.

BACKGROUND OF THE INVENTION

Alpha adrenergic receptors are plasma membrane receptors which are located in the peripheral and central nervous systems throughout the body. They are members of a diverse family of structurally related receptors which contain seven putative helical domains and transduce signals by coupling to guanine nucleotide binding proteins (G-proteins).

The alpha adrenergic receptor family of adrenergic receptors (AR) consists of two groups: alpha-1 and alpha-2. Of the alpha-2 group, there are three distinct subtypes denoted alpha-2A, alpha-2B and alpha-2C. The subtypes are derived from different genes, have different structures, unique distributions in the body, and specific pharmacologic properties. (Due to localization of the genes to human chromosomes 10, 2 and 4, the alpha-2A, alpha-2B, and alpha-2C receptors have sometimes been referred to as alpha-2C10, alpha-2C2 and alpha-2C4 receptors, respectively). Like other adrenergic receptors, the alpha-2 receptors are activated by endogenous agonists such as epinephrine (adrenaline) and norepinephrine (noradrenaline), and synthetic agonists, which promote coupling to G-proteins that in turn alter effectors such as enzymes or channels.

The alpha-2 receptors couple to the $G_i$ and $G_o$ family of G-proteins. Alpha-2 receptors modulate a number of effector pathways in the cell: inhibition of adenylyl cyclase (decreases cAMP), stimulation of mitogen activated protein (MAP) kinase, stimulation of inositol phosphate accumulation, inhibition of voltage gated calcium channels and opening of potassium channels. (Limbird, L. E. (1988) *FASEB J* 2, 2686–2695, Luttrell, L. M., van Biesen, T., Hawes, B. E., Della Rocca, G. J., and Luttrell, D. K., and Lefkowitz, R. J. (1998) in *Catecholamines: Bridging Basic Science with Clinical Medicine* (Goldstein, D. S., Eisenhofer, G., and McCarty, R., eds pp. 466–470, Academic Press). The alpha-2 receptors are expressed on many cell-types in multiple organs in the body including those of the central and peripheral nervous systems.

Alpha-2BAR have a distinct pattern of expression within the brain, liver, lung, and kidney, and recent studies using gene knockouts in mice have shown that disruption of this receptor effects mouse viability, blood pressure responses to alpha-2-AR agonists, and the hypertensive response to salt loading. See Link, R. E., Desai, K., Hein, L., Stevens, M. E., Chruscinski, A., Bernstein, D., Barsh, G. S., and Kobilka, B. K. (1996) *Science* 273, 803–805; Makaritsis, K. P., Handy, D. E., Johns, C., Kobilka, B., Gavras, I., and Gavras, H. (1999) *Hypertension* 33, 14–17).

It is known that the alpha-2BAR undergoes short-term agonist promoted desensitization (Eason, M. G. and Liggett, S. B. (1992) *J. Biol. Chem.* 267, 25473–25479). This desensitization is due to phosphorylation of the receptor, which evokes a partial uncoupling of the receptor from functional interaction with $G_i/G_o$ (Jewell-Motz, E. A. and Liggett, S. B. (1995) *Biochem* 34, 11946–11953; Kurose, H. and Lefkowitz, R. J. (1994) *J. Biol. Chem.* 269, 10093–10099). Such phosphorylation appears to be due to G protein coupled receptor kinases (GRKs), a family of serine/threonine kinases which phosphorylate the agonist-occupied conformations of many G-protein coupled receptors (Pitcher, J. A., Freedman, N. J., and Lefkowitz, R. J. (1998) *Annu Rev Biochem* 67, 692). The phosphorylation process serves to finely regulate receptor function providing for rapid adaptation of the cell to its environment. Desensitization may also limit the therapeutic effectiveness of administered agonists. For the $\alpha_{2B}$AR, phosphorylation of serines/threonines in the third intracellular loop of the receptor is dependent on the presence of a stretch of acidic residues in the loop that appears to establish the milieu for GRK function (Jewell-Motz, E. A. and Liggett, S. B. (1995) *Biochem* 34, 11946–11953).

There has been a considerable research effort to clone and sequence the alpha-2AR. For example, the gene encoding the alpha-2A, alpha-2B, alpha-2C subtypes has been cloned and sequenced. (Kobilka et al. *Science* 238, 650–656 (1987); Regan et al., Lomasney et al. *Proc. Nat. Acad. Sci.* 87, 5094–5098 (1994)). These receptors have also been named as alpha-2C10, alpha-2C2 and alpha-2C4, according to their location on chromosomes 10, 4 and 2.

A polymorphism occurring in the gene encoding the alpha-2BAR has been previously reported. This polymorphism has been described as a deletion of three glutamic acid residues in a highly acidic stretch of amino acids in the third intracellular loop of the receptor. (Heinonen, P., Koulu, M., Pesonen, U., Karvonen, M. K., Rissanen, A., Laakso, M., Valve, R., Uusitupa, M., and Scheinin, M. (1999) *J Clin Endocrinol Metab* 84, 2429–2433; Baldwin, C. T., Schwartz, F., Baima, J., Burzstyn, M., DeStefano, A. L., Gavras, I., Handy, D. E., Joost, O., Martel, T., Manolis, A., Nicolaou, M., Bresnahan, M., Farrer, L., and Gavras, H. (1999) *Am J Hypertens* 12, 853–857). However, no pharmacologic studies have been carried out to determine if this polymorphism alters receptor function.

Given the importance of the alpha-2BAR in modulating a variety of physiological functions, there is a need in the art for improved methods to identify polymorphisms and to correlate the identity of these polymorphisms with signaling functions of alpha-2BAR. The present invention addresses these needs and more by providing polynucleotide and amino acid polymorphisms, molecules, and methods for detecting, genotyping and haplotyping the polymorphisms in the alpha-2BAR. The present invention is useful for determining an individual's risk for developing a disease, assist the clinician in diagnosing and prognosing the disease.

The present invention also provides methods for selecting appropriate drug treatment based on the identity of such polymorphism.

SUMMARY OF THE INVENTION

The present invention is directed to molecules useful for detecting one or more polymorphic sites in polynucleotides encoding the alpha-2B adrenergic receptor gene and gene products.

In one embodiment, the present invention provides a method of detecting a polymorphic site in a sample to determine alpha-2B adrenergic receptor function, comprising: (a) obtaining the sample having a polynucleotide encoding an alpha-2B-adrenergic receptor molecule comprising SEQ ID NO: 1 or 2 or fragment or complement of the polynucleotide; and (b) detecting in the sample a polymorphic site comprising nucleotide positions 901 to 909 of SEQ ID NO: 1 or 2 or fragment or complement thereof.

In a second embodiment, the present invention provides a method of detecting a polymorphic site in a sample to determine alpha-2B-adrenergic receptor function, comprising: (a) obtaining the sample having an alpha-2B-adrenergic receptor molecule comprising amino acid SEQ ID NO: 7 or 8 or fragment thereof; and (b) detecting in the sample the polymorphic site at amino acid positions 294 to 309 of SEQ ID NO: 7 or 8.

In a third embodiment, the present invention provides a method of genotyping an alpha-2B adrenergic receptor gene comprising: (a) obtaining a sample having a polynucleotide encoding an alpha-2B-adrenergic receptor molecule comprising SEQ ID NO: 1 or 2 or fragment or complement of the polynucleotide; and (b) detecting in the sample a polymorphic site comprising nucleotide positions 901 to 909 of SEQ ID NO: 1 or 2 or fragment or complement thereof.

In one exemplary embodiment, the present invention provides a method of detecting a polymorphic site in a sample to determine alpha-2B adrenergic receptor function, comprising: (a) obtaining the sample having a polynucleotide encoding an alpha-2B-adrenergic receptor molecule comprising SEQ ID NO: 1 or 2 or fragment or complement of the polynucleotide; and (b) detecting in the sample a polymorphic site comprising nucleotide positions 901 to 909 of SEQ ID NO: 1 or 2 or fragment or complement thereof.

In a second exemplary embodiment, the present invention provides a method of haplotyping an alpha-2B adrenergic receptor gene comprising: a. obtaining a sample having a polynucleotide encoding an alpha-2B-adrenergic receptor molecule comprising SEQ ID NO: 1 or 2 or fragment or complement of the polynucleotide; b. detecting in the sample a polymorphic site comprising nucleotide positions 901 to 909 of SEQ ID NO: 1 or 2 or fragment or complement thereof on one copy of the alpha-2B-adrenergic receptor gene; and c. determining the identity of an additional polymorphic site on the copy of the alpha-2B-adrenergic receptor gene.

In a third exemplary embodiment, the present invention provides a method for determining an individual at increased risk for developing a disease associated with an alpha-2B adrenergic receptor molecule comprising: a. obtaining a sample having a polynucleotide encoding an alpha-2B-adrenergic receptor molecule comprising SEQ ID NO: 1 or 2 or fragment or complement of the polynucleotide from the individual; and b. detecting in the sample a polymorphic site comprising nucleotide positions 901 to 909 of SEQ ID NO: 1 or 2 or fragment or complement thereof which correlates to the disease, thereby identifying the individual at increased risk for the disease.

In another embodiment, the present invention provides a method for diagnosing or prognosing an individual with a disease associated with an alpha-2B adrenergic receptor molecule, comprising a. obtaining a sample having a polynucleotide encoding an alpha-2B-adrenergic receptor molecule comprising SEQ ID NO: 1 or 2 or fragment or complement of the polynucleotide from the individual; and b. detecting in the sample a polymorphic site comprising nucleotide positions 901 to 909 of SEQ ID NO: 1 or 2 or fragment or complement thereof which correlates to the disease, thereby diagnosing or prognosing the disease.

In still another embodiment, the present invention provides a method of predicting an individual's response to an agonist or antagonist, comprising: a. obtaining a sample having a polynucleotide encoding an alpha-2B-adrenergic receptor molecule comprising SEQ ID NO: 1 or 2 or fragment or complement of the polynucleotide from the individual; b. detecting in the sample a polymorphic site comprising nucleotide positions 901 to 909 of SEQ ID NO: 1 or 2 or fragment or complement thereof; and c. correlating the polymorphic site to a predetermined response thereby predicting the individual's response to the agonist or antagonist.

In yet another embodiment, the present invention provides a method for selecting an appropriate pharmaceutical composition to administer to an individual having a disease associated with an alpha-2B adrenergic receptor molecule, comprising: a. obtaining a sample having a polynucleotide encoding an alpha-2B-adrenergic receptor molecule comprising SEQ ID NO: 1 or 2 or fragment or complement of the polynucleotide from the individual; b. detecting in the sample a polymorphic site comprising nucleotide positions 901 to 909 of SEQ ID NO: 1 or 2 or fragment or complement thereof, and c. selecting the appropriate pharmaceutical composition based on the polymorphic site present.

In a preferred embodiment, the present invention provides a method of detecting a polymorphic site in a sample to determine alpha-2B-adrenergic receptor function, comprising: a. obtaining the sample having a polynucleotide encoding an alpha-2B-adrenergic receptor molecule comprising SEQ ID NO: 1 or 2 or fragment or complement of the polynucleotide; and b. indirectly detecting in the sample a polymorphic site comprising nucleotide positions 901 to 909 of SEQ ID NO: 1 or 2 or fragment or complement thereof.

In a second preferred embodiment, the present invention provides a method of detecting a polymorphic site in a sample to determine alpha-2B-adrenergic receptor function, comprising: a. obtaining the sample having an alpha-2B-adrenergic receptor molecule comprising amino acid SEQ ID NO: 7 or 8 or fragment thereof; and b. indirectly detecting in the sample the polymorphic site at amino acid positions 294 to 309 of SEQ ID NO: 7 or 8.

For a better understanding of the present invention together with other and further advantages and embodiments, reference is made to the following description taken in conjunction with the examples, the scope of which is set forth in the appended claims.

BRIEF DESCRIPTION OF THE DRAWINGS

Preferred embodiments of the invention have been chosen for purposes of illustration and description, but are not intended in any way to restrict the scope of the invention.

The preferred embodiments of certain aspects of the invention are shown in the accompanying figures, wherein.

DETAILED DESCRIPTION OF THE INVENTION

Alpha-2B Adrenergic Receptor Function

Figure 1:
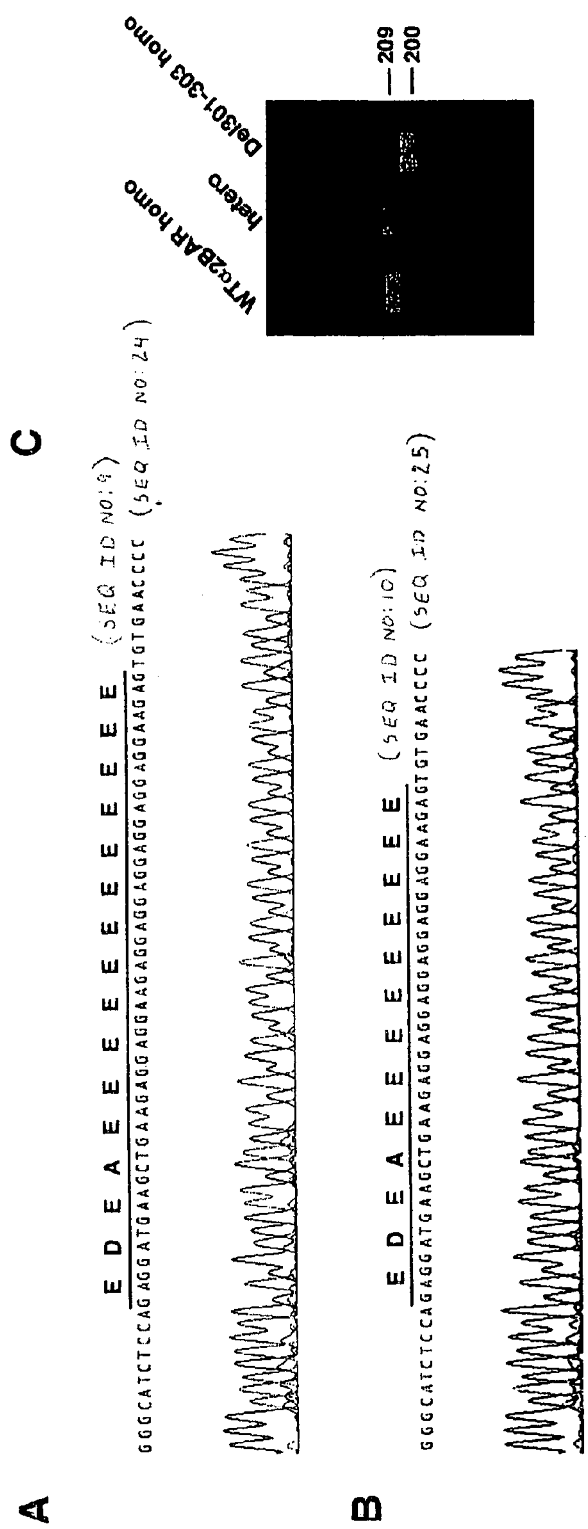
FIG. 1 illustrates identification of the human alpha-2BAR variant. Shown in Panels A and B are representative automated sequence chromatograms identifying a deletion of the nucleotides GAAGAGGAG (SEQ ID NO: 3). Panel C illustrates a rapid screening technique that identifies homozygous and heterozygous PCR products by size.

The alpha-2B adrenergic receptor is localized at the cell membrane and serves as a receptor for the endogenous catecholamine agonists i.e., epinephrine and norepinephrine, and synthetic agonists and antagonists. Upon binding of the agonist, the receptor stabilizes in a conformation that favors contact with all activation of certain heterotrimeric G proteins. These include $G_{i1}$, $G_{i2}$, $G_{i3}$ and $G_o$. The $G_i$ G protein alpha subunits serve to decrease the activity of the enzyme adenylyl cyclase, which lowers the intracellular levels of cAMP (a classic second messenger). The alpha subunits, and/or the beta-gamma subunits of these G proteins also act to activate MAP kinase, open potassium channels, inhibit voltage gated calcium channels, and stimulate inositol phosphate accumulation. The physiologic consequences of the initiation of these events include inhibition of neurotransmitter release from central and peripheral noradrenergic neurons.

Alpha-2BARs are expressed in the brain, liver, lung, and kidney. Studies using gene knockouts in mice have shown that disruption of this receptor effects mouse viability, blood pressure responses to alpha-2-AR agonists, and the hypertensive response to salt loading. Alpha-2BAR when stimulated cause vasoconstriction.

Alpha-2BARs undergoes short-term agonist promoted desensitization. This desensitization is due to phosphorylation of the receptor, which evokes a partial uncoupling of the receptor from functional interaction with $G_i/G_o$. Such phosphorylation appears to be due to GRKs, a family of serine/threonine kinases which phosphorylate the agonist-occupied conformations of many G-protein coupled receptors. Desensitization may also limit the therapeutic effectiveness of administered agonists. For the alpha-2BAR, phosphorylation of serines/threonines in the third intracellular loop of the receptor is dependent on the presence of a stretch of acidic residues in the loop that appears to establish the milieu for GRK function (Jewell-Motz, E. A. and Liggett, S. B. (1995) *Biochem* 34, 11946–11953).

Since most organs have innervation by these neurons, the alpha-2B receptor activity can alter processes in many organ systems. Of particular therapeutic interest has been the development of highly subtype-specific alpha-2 agonists and antagonists. Such compounds, then, can selectively block or activate one subtype, such as the alpha-2B, without affecting the others. This would provide for highly specific responses without side-effects from activating the other subtypes.

Alpha-2B adrenergic receptor molecule function or activity can be measured by methods known in the art. Some examples of such measurement include radio-ligand binding to the alpha-2B adrenergic receptor molecule by an agonist or antagonist, receptor-G protein binding, stimulation or inhibition of adenyly cyclase, MAP kinase, phosphorylation or inositol phosphate (IP3). However, the polymorphisms of the present invention (discussed below) alter alpha-2B adrenergic receptor molecule function or activity.

In one embodiment of the present invention, the DEL301–303 polymorphism showed depressed phosphorylation resulting in loss of short-term agonist-promoted receptor desensitization in the alpha-2BAR molecule. The DEL301–303 polymorphism also showed altered or decreased receptor coupling.

Alpha-2B Adrenergic Receptor Diseases

Alpha-adrenergic receptors play an important role in regulating a variety of physiological functions because of their distribution in many organs of the body and the brain. Thus, dysfunctional alpha-2B receptors can predispose to, or modify, a number of diseases or alter response to therapy. The present invention stems in part from the recognition that certain polymorphisms in the alpha-2BAR result in receptor molecules with altered functions. These altered functions put an individual at risk for developing diseases associated with the alpha-2BAR. As used herein, "disease" includes but is not limited to any condition manifested as one or more physical and/or psychological symptoms for which treatment is desirable, and includes previously and newly identified diseases and other disorders. Such diseases include cardiovascular diseases such as hypertension, hypotension, congestive heart failure, arrhythmias, stroke, myocardial infarction, neurogenic and obstructive peripheral vascular disease, ischemia-reperfusion damage and intermittent claudication, migraine, metabolic rate and combinations thereof. Central nervous systems (CNS) diseases are also contemplated by the present invention. Some examples of CNS diseases include Parkinsonism, Alzheimers, attention deficit disorder, hyperreactivity, anxiety, manic-depression and combinations thereof. Since the alpha-2B controls certain central nervous system and peripheral functions as discussed above, dysfunctional polymorphisms are likely to be important in as of yet unclassified disorders of memory and behavior.

In one embodiment, the present invention includes methods of determining the risk an individual has for developing a disease. Alternatively, the present invention can be used to diagnose or prognose an individual with a disease. For example, a polymorphic site in the polynucleotide encoding the mutant alpha-2BAR identified as SEQ ID NO: 2, such as for example, nucleotide positions 901 to 909 can be detected. This polymorphic site corresponds to GAGGAGGAG (SEQ ID NO: 4). Thus, the mutant receptor has a deletion of nine nucleotides (DEL901–909) GAAGAGGAG (SEQ ID NO: 3) when compared to the polynucleotide encoding the wild-type alpha-2BAR (IN901–909). This exemplified polymorphism results in amino acid deletions at positions 301 to 303 of the mutant alpha-2B adrenergic receptor molecule resulting in the mutant receptor identified as SEQ ID NO: 8. More particularly, the preferred polymorphism results in a deletion of 3 glutamic acids at amino acid positions 301 to 303 (DEL 301–303) of the alpha-2B adrenergic receptor molecule resulting in a receptor with decreased alpha-agonist function. Such polymorphism can be correlated to increasing an individual's risk for developing a disease, or can be used to determine a diagnosis or prognosis for the disease.

In another embodiment of the present invention, a polymorphic site in SEQ ID NO: 1, such as for example, nucleotide position 901 to 909 can be detected. This polymorphic site corresponds to (IN901–909) GAAGAGGAG (SEQ ID NO: 3) that is an insertion of these nine nucleotides compared to the polynucleotide encoding the mutant alpha-2BAR. This exemplified polymorphism results in amino acid insertion at positions 301 to 303 (IN301–303) of the alpha-2B adrenergic receptor molecule resulting in the wild-type receptor identified as SEQ ID NO: 7. More particularly, the preferred polymorphism results in an insertion of 3 glutamic acids at amino acid positions 301 to 303 of the alpha-2B adrenergic receptor molecule resulting in a receptor with increased alpha-agonist function and increased agonist-promoted desensitization. Such polymorphism can be correlated to decreasing an individual's risk for developing a disease, or can be used to determine a diagnosis or prognosis for the disease.

As used herein, "diagnosis" includes determining the nature and cause of the disease, based on signs and symptoms of the disease and laboratory finding. One such laboratory finding is the identification of at least one polymorphism in nucleic acids encoding the alpha-2BAR. Prognosis of a disease includes determining the probable clinical course and outcome of the disease. Increased risk for the disease includes an individual's propensity or probability for developing the disease.

The terms "correlate the polymorphic site with a disease" includes associating the polymorphism which occurs at a higher allelic frequency or rate in individuals with the disease than individuals without the disease. Correlation of the disease with the polymorphism can be accomplished by bio-statistical methods known in the art, such as for example, by Chi-squared tests or other methods described by L. D. Fisher and G. vanBelle, *Biostatistics: A Methodology for the Health Sciences*, Wiley-Interscience (New York) 1993.

Preferably, the identity of at least one polymorphic site in an alpha-2B adrenergic receptor molecule is determined. Generally, in performing the methods of the present invention, the identity of more than one polymorphic site is determined. As used herein a polymorphic site includes one or more nucleotide deletions, insertions, or base changes at a particular site in a nucleic acid sequence. In some preferred embodiments, the identity of between about two and about six polymorphic sites are determined, though the identification of other numbers of sites is also possible. Most preferably, the polymorphisms and molecules of the present invention are utilized in determining the identity of at least one polymorphic site of the alpha-2BAR molecule and using that identity as a predictor of increased risk for developing a disease. The type of polymorphism present can also dictate the appropriate drug selection. In other embodiments, the polymorphisms and molecules of the present are used for diagnosing or prognosing an individual with a disease associated with an alpha-2BAR molecule.

Alpha-2B Adrenergic Receptor Polymorphisms

The particular gene sequences of interest to the present invention comprise "mutations" or "polymorphisms" in the genes encoding the alpha-2B adrenergic receptor. The genomes of animals and plants naturally undergo spontaneous mutation in the course of their continuing evolution (J. F. Gusella (1986) *Ann. Rev. Biochem.* 55:831–854). These mutations may be in the form of deletions, insertions, or base changes at a particular site in a nucleic acid sequence. This altered sequence and the initial sequence may co-exist in a species' population. In some instances, these changes confer neither an advantage or a disadvantage to the species and multiple alleles of the sequence may be in stable or quasistable equilibrium. In some instances, however, these sequence changes will confer a survival or evolutionary advantage to the species, and accordingly, the altered allele may eventually (i.e. over evolutionary time) be incorporated into the genome of many or most members of that species. In other instances, the altered sequence confers a disadvantage to the species, as where the mutation causes or predisposes an individual to a genetic disease. As used herein, the terms "mutation" or "polymorphism" refer to the condition in which there is a variation in the DNA sequence between some members of a species. Typically, the term "mutation" is used to denote a variation that is uncommon (less than 1%), a cause of a rare disease, and that results in a gene that encodes a non-functioning protein or a protein with a substantially altered or reduced function. Such mutations or polymorphisms include, but are not limited to, single nucleotide polymorphisms (SNPs), one or more base deletions, and one or more base insertions.

Polymorphisms may be synonymous or nonsynonymous. Synonymous polymorphisms when present in the coding region typically do not result in an amino acid change. Nonsynonymous polymorphism when present in the coding region alter one or more codons resulting in an amino acid replacement in the amino acid chain. Such mutations and polymorphisms may be either heterozygous or homozygous within an individual. Homozygous individuals have identical alleles at one or more corresponding loci on homologous chromosomes. While heterozygous individuals have two different alleles at one or more corresponding loci on homologous chromosomes. A polymorphism is thus said to be "allelic," in that, due to the existence of the polymorphism, some members of a species carry a gene with one sequence (e.g., the original or wild-type "allele"), whereas other members may have an altered sequence (e.g., the variant or, mutant "allele"). In the simplest case, only one mutated variant of the sequence may exist, and the polymorphism is said to be diallelic. For example, if the two alleles at a locus are indistinguishable in their effects on the organism, then the individual is said to be homozygous at the locus under consideration. If the two alleles at a locus are distinguishable because of their differing effects on the organism, then the individual is said to be heterozygous at the locus. In the present application, typographically, alleles are distinguished + and −. Using these symbols, homozygous individuals are +/+, or −/−. Heterozygous individuals are +/−. The occurrence of alternative mutations can give rise to triallelic and tetra-allelic polymorphisms, etc. An allele may be referred to by the nucleotide(s) that comprise the mutation.

The wild-type gene encoding the third intracellular loop of the human alpha-2B receptor molecule is disclosed in GenBank Accession No. # AF005900, the entire disclosure is herein incorporated by reference. As used herein, the term "gene" includes a segment of DNA that contains all the information for the regulated biosynthesis of an RNA product, including promoters, exons, introns, and other untranslated regions that control expression.

The terms "alpha-2B-adrenergic receptor polymorphism" or "alpha-2BAR polymorphism", are terms of art and refer to at least one polymorphic site in the polynucleotide or amino acid sequence of an alpha-2B adrenergic receptor gene or gene product. For purposes of the present application, the wild-type polynucleotide encoding the alpha-2B-adrenergic receptor is designated SEQ ID NO: 1 and the wild-type gene product comprising the alpha-2B-adrenergic receptor molecule, is designated amino acid SEQ ID NO: 7.

Those in the art will readily recognize that nucleic acid molecules may be double-stranded molecules and that reference to a particular site on one strand refers, as well, to the corresponding site on a complementary strand. Thus, in defining a polymorphic site, reference to an adenine, a thymine (uridine), a cytosine, or a guanine at a particular site on the plus (sense) strand of a nucleic acid molecule is also intended to include the thymine (uridine), adenine, guanine, or cytosine (respectively) at the corresponding site on a minus (antisense) strand of a complementary strand of a nucleic acid molecule. Thus, reference may be made to either strand and still comprise the same polymorphic site and an oligonucleotide may be designed to hybridize to either strand. Throughout this specification, in identifying a polymorphic site, reference is made to the sense strand, only for the purpose of convenience.

Preferred polymorphisms of the present invention occur in the gene encoding the alpha-2B adrenergic receptor molecule identified as SEQ ID No: 1 or 2 or fragments thereof or complements thereof.

For the purposes of identifying the location of at least one polymorphism or polymorphic site, the first nucleotide of the start codon of the coding region (the adenine of the ATG in a DNA molecule and the adenine of the AUG in an RNA molecule) of the alpha-2BAR gene is considered nucleotide "1." This corresponds to nucleotide 1 of SEQ ID NO: 1 or 2. The end of the coding region corresponds to adenine at position 1353 for SEQ ID NO: 1. The end of the coding region corresponds to adenine at position 1344 for SEQ ID NO: 2. According to the present invention, polymorphisms can occur any where in the coding region identified as SEQ ID NO: 1 or 2.

For example, the polymorphism occurring in the polynucleotide encoding the wild-type alpha-2BAR molecule (identified as SEQ ID NO: 1) is a nine nucleotide base insertion (IN901–909) at nucleotide positions 901 to 909 of SEQ ID NO: 1. This nine nucleotide base insertion is identified as GAAGAGGAG (SEQ ID NO: 3) and is a polymorphic site or fragment (FIG. 1A) of SEQ ID NO: 1. A compliment to this polymorphic site includes CTTCTCCTC (SEQ ID NO: 5).

In another embodiment of the present invention, at least one polymorphic site has been identified in the polynucleotide encoding the mutant alpha-2BAR identified as SEQ ID NO: 2. This polymorphic site is a nine nucleotide deletion at nucleotide positions 901 to 909 (DEL901–909). This polymorphic site shifts GAGGAGGAG (SEQ ID NO: 4) into nucleotide positions 901 to 909. Thus, the polynucleotide encoding the mutant receptor has a deletion of nine nucleotides (FIG. 1B) GAAGAGGAG (SEQ ID NO: 3) when compared to the polynucleotide encoding the wild-type alpha-2BAR (identified as SEQ ID NO: 1). A compliment to the GAGGAGGAG (SEQ ID NO: 4) polymorphic site includes CTCCTCCTC (SEQ ID NO: 6).

An insertion or deletion polymorphisms can change the exact position of at least one polymorphic site with respect to the polynucleotide encoding the alpha2-BAR identified as SEQ ID NO: 1 or 2. The present invention includes polymorphic sites occurring downstream of the IN/DEL901–909 polymorphic site. For example, detecting one or more a single nucleotide polymorphisms (SNP) such as G at nucleotide position 915 and/or G at 951, will indicate the IN901–909 polymorphism. Alternately, the end of the coding region of the polynucleotide can be probed to determine the longer polynucleotide indicating the IN901–909 polymorphism. For example, if a G SNP is detected at nucleotide position 1345, this indicates, the IN901–909 polymorphism of SEQ ID NO: 1, since the mutant SEQ ID NO: 2 does not have this nucleotide position in the coding region. Thus, the IN/DEL901–909 polymorphic site can indirectly be detected by the nucleotide shift resulting from the insertion or deletion.

As used herein, "fragments" include less than the entire nucleotide sequence of SEQ ID NO:1 or 2. Preferred fragments comprise the IN901–909 or DEL901–909 polymorphic site. In order for a nucleic acid sequence to be a fragment, it must be readily identifiable by the molecular techniques as discussed such as with nucleic acid probes.

The polymorphisms of the present invention can occur in the translated alpha-2B adrenergic receptor molecule as well. For example, the first amino acid of the translated protein product or gene product (the methionine) is considered amino acid "1" in the wild-type alpha-2B adrenergic receptor molecule designated amino acid SEQ ID NO: 7. The end of the receptor corresponds to tryptophan at amino acid position 450 for SEQ ID NO: 7. Polymorphisms can occur anywhere in SEQ ID NO: 7. The wild-type alpha-2B adrenergic receptor molecule (FIG. 2) comprises an insertion of 3 glutamic acids at amino acid positions 301 to 303 (IN301–303) of the alpha-2B adrenergic receptor molecule designated EEE (SEQ ID NO: 11). Thus, in the stretch of amino acids at positions 294–309 identified as EDEAEEEEEEEEEEEE (SEQ ID NO: 9), there is an insertion of three additional glutamic acids when compared to the mutant alpha-2B adrenergic receptor molecule. Accordingly, EDEAEEEEEEEEEEEE (SEQ ID NO: 9) and EEE (SEQ ID NO: 11) are examples of polymorphic sites occurring in SEQ ID NO: 7.

Figure 2:
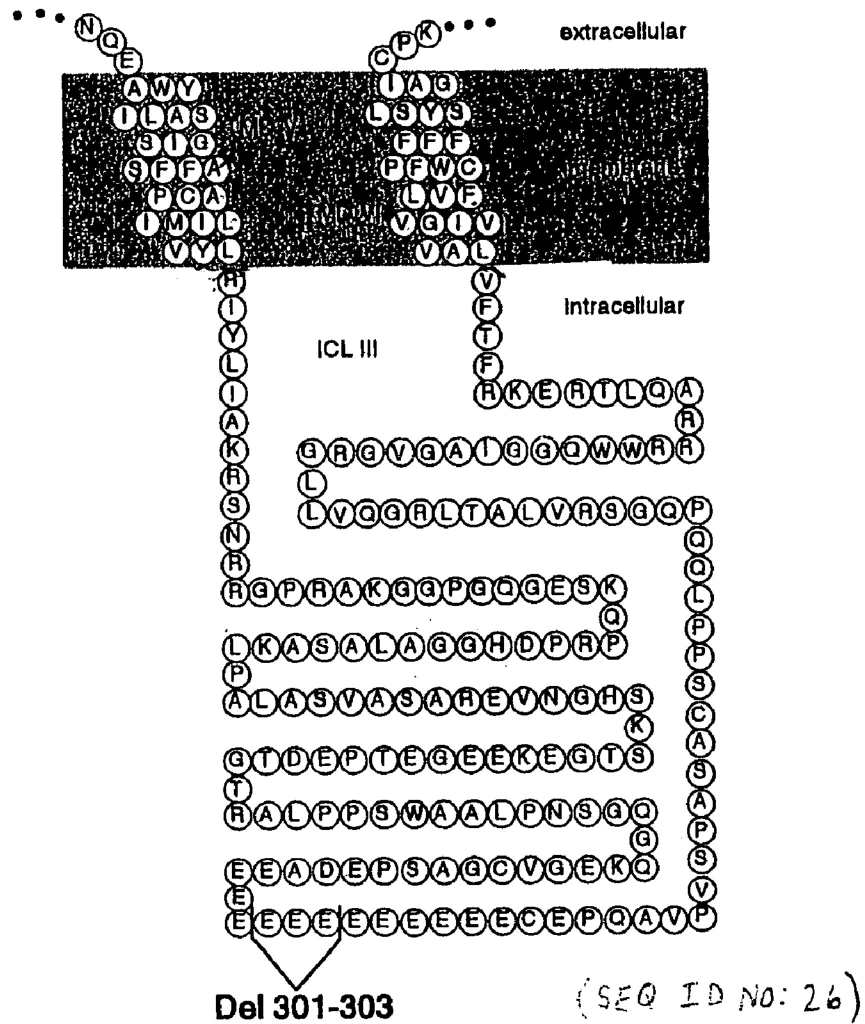
FIG. 2 illustrates localization of the expressed alpha-2BAR polymorphism. Shown is the fifth and sixth transmembrane spanning domain (TMD) and the third intracellular loop of the receptor.

In another embodiment of the present invention, SEQ ID NO: 8 comprises the entire mutant amino acid sequence of alpha-2B adrenergic receptor molecule with deletion of EEE at amino acid positions 301–303 (DEL301–303) (shown in FIG. 2). The first amino acid of the translated protein product or gene product (the methionine) is considered amino acid "1" in the mutant alpha-2B adrenergic receptor molecule designated amino acid SEQ ID NO: 8. The end of the receptor corresponds to tryptophan at amino acid position 447 for SEQ ID NO: 8. Polymorphisms can occur anywhere in the amino acid sequence designated SEQ ID NO: 8. For example, the mutant alpha-2B adrenergic receptor molecule comprises a deletion of EEE (SEQ ID NO: 11) or 3 glutamic acids in the mutant alpha-2B adrenergic receptor molecule. Thus, in the stretch of amino acids at positions 294–306 identified as EDEAEEEEEEEEE (SEQ ID NO: 10). There is a deletion of three glutamic acids when compared to the wild-type alpha-2B adrenergic receptor molecule. Accordingly, EDEAEEEEEEEEEEEE (SEQ ID NO: 10) and EEE (SEQ ID NO: 11) are examples of polymorphic sites occurring in SEQ ID NO: 8.

Since the mutant alpha-2B adrenergic receptor molecule has DEL301–303, the rest of the molecule shifts causing amino acids 307, 308 and 309 to have CEP at these positions in the mutant receptor. Thus, another polymorphic site is CEP (SEQ ID NO: 12) at amino acid positions 307–309 of SEQ ID NO: 8, individually and/or collectively, these positions represent polymorphic sites when compared to the wild-type receptor. Alternatively, the mutant alpha-2B adrenergic receptor molecule lacks amino acids positions 448, 449 and 450. Thus, these are also polymorphic sites.

For example, an insertion or deletion polymorphisms can change the exact position of at least one polymorphic site with respect to the amino sequence of the alpha-2-BAR identified as SEQ ID NO: 7 or 8. The present invention includes one or more polymorphic sites occurring downstream of the IN/DEL301–303 polymorphic site. For example, detecting R at amino position 340 and/or R at 438, will indicate the IN301–303 polymorphism. Alternately, the end of the coding region of the polynucleotide can be probed to determine the longer chain of amino acids indicating the IN301–303 polymorphism. For example, if a T is detected at amino acid position 448, this indicates the wild-type IN301–303 polymorphism of SEQ ID NO: 7, since the mutant SEQ ID NO: 8 does not have this amino acid position with regards to the encoded gene product. Thus, the IN/DEL301–303 can be indirectly detected by detecting one or more amino acid positions downstream of IN/DEL301–303 polymorphic site.

The present invention includes fragments of gene products. Preferred gene product fragments include less than the entire amino acid sequence of SEQ ID NO: 7 or 8. Preferred gene product fragments comprise the IN301–303 or DEL301–303 polymorphic site. In order for an amino acid sequence to be a fragment, it must be readily identifiable by molecular and pharmacological techniques discussed below, such as for example, ligand binding.

The present invention includes homologs and fragments of the nucleic acids that encode alpha2-BAR. To be considered a homolog or active fragment, the sequence of an amino acid or a nucleic acid must satisfy two requirements. In the present specification, the sequence of a first nucleotide sequence (SEQ ID NO: 1 or 2) is considered homologous to that of a second nucleotide sequence if the first sequence is at least about 30% identical, preferably at least about 50% identical, and more preferably at least about 65% identical to the second nucleotide sequence. In the case of nucleotide sequences having high homology, the first sequence is at least about 75%, preferably at least about 85%, and more preferably at least about 95% identical to the second nucleotide sequence.

The amino acid sequence of a first protein (SEQ ID NO: 7 or 8) is considered to be homologous to that of a second protein if the amino acid sequence of the first protein shares at least about 20% amino acid sequence identity, preferably at least about 40% identity, and more preferably at least about 60% identity, with the sequence of the second protein. In the case of proteins having high homology, the amino acid sequence of the first protein shares at least about 75% sequence identity, preferably at least about 85% identity, and more preferably at least about 95% identity, with the amino acid sequence of the second protein.

In order to compare a first amino acid or nucleic acid sequence to a second amino acid or nucleic acid sequence for the purpose of determining homology, the sequences are aligned so as to maximize the number of identical amino acid residues or nucleotides. The sequences of highly homologous proteins and nucleic acid molecules can usually be aligned by visual inspection. If visual inspection is insufficient, other methods of determining homology are known in the art. For example, the proteins may be aligned in accordance with the FASTA method in accordance with Pearson et al. (1988). Preferably, any of the methods described by George et al., in Macromolecular Sequencing and Synthesis, Selected Methods and Applications, (1988).

A second test for homology of two nucleic acid sequences is whether they hybridize under normal hybridization conditions, preferably under stringent hybridization conditions. Also included in the invention are proteins that are encoded by nucleic acid molecules that hybridize under high stringent conditions to a sequence complementary to SEQ ID NO: 1 or 2. The term "stringent conditions," as used herein, is equivalent to "high stringent conditions" and "high stringency". These terms are used interchangeably in the art. High stringent conditions are defined in a number of ways. In one definition, stringent conditions are selected to be about 50° C. lower than the thermal melting point (Tm) for a specific sequence at a defined ionic strength and pH. The Tm is the temperature (under defined ionic strength and pH) at which 50% of the target sequence hybridizes to a perfectly matched sequence. Typical stringent conditions are those in which the salt concentration is at least about 0.02 M at pH 7 and the temperature is at least about 60° C. "Stringent conditions," in referring to homology or substantial similarity in the hybridization context, can be combined conditions of salt, temperature, organic solvents or other parameters that are typically known to control hybridization reactions. The combination of parameters is more important than the measure of any single parameter. If incompletely complementary sequences recognize each other under high stringency conditions, then these sequences hybridize under conditions of high stringency. See U.S. Pat. No. 5,786,210; Wetmur and Davidson J. Mol. Biol. 31:349–370 (1968). Control of hybridization conditions, and the relationships between hybridization conditions and degree of homology are understood by those skilled in the art. See, e.g., Sambrook, J. et al. (Eds.), Molecular Cloning, Second Edition, Cold Spring Harbor Laboratory Press, Cold Spring Harbor, N.Y. (1989) and Ausubel, F. M. et al. (Eds.), Current Protocols in Molecular Biology, John Wiley & Sons, New York (1999).

Substitutions, additions, and/or deletions in an amino acid sequence can be made as long as the protein encoded by the nucleic acid of the invention continues to satisfy the functional criteria described herein. An amino acid sequence that is substantially the same as another sequence, but that differs from the other sequence by means of one or more substitutions, additions, and/or deletions, is considered to be an equivalent sequence. Preferably, less than 50%, more preferably less than 25%, and still more preferably less than 10%, of the number of amino acid residues in a sequence are substituted for, added to, or deleted from the protein encoded by the nucleic acid of the invention.

Alpha-2B Adrenergic Receptor Molecules

The molecules of the present invention are particularly relevant to determine increased risk an individual has for a disease and/or response to therapy. The molecules of the present invention can also be used to diagnosis and prognosis a disease.

The molecules of the present invention will preferably be "biologically active" with respect to either a structural attribute, such as the capacity of a nucleic acid to hybridize to another nucleic acid molecule or to be used by a polymerase as a primer. Alternatively, such an attribute may be catalytic, and thus involve the capacity of the agent to mediate a chemical reaction or response.

A preferred class of molecules of the present invention comprise adrenergic receptor molecules. Preferably, alpha-2B-adrenergic receptor molecules. Such molecules may be either DNA or RNA, single-stranded or double-stranded. Alternatively, such molecules may be proteins and antibodies. Such molecules may also be fragments, portions, and segments thereof and molecules, such as oligonucleotides, that specifically hybridize to nucleic acid molecules encoding the alpha-2B-adrenergic receptor. Such molecules may be isolated, derived, or amplified from a biological sample. Alternatively, the molecules of the present invention may be chemically synthesized. The term "isolated" as used herein refers to the state of being substantially free of other material such as nucleic acids, proteins, lipids, carbohydrates, or other materials such as cellular debris or growth media with which the alpha-2B-adrenergic receptor molecule, polynucleotide encoding the alpha-2B-adrenergic receptor molecule, primer oligonucleotide, or allele-specific oligonucleotide may be associated. Typically, the term "isolated" is not intended to refer to a complete absence of these materials. Neither is the term "isolated" generally intended to refer to water, buffers, or salts, unless they are present in amounts that substantially interfere with the methods of the present invention. The term "sample" as used herein generally refers to any material containing nucleic acid, either DNA or RNA or amino acids. Generally, such material will be in the form of a blood sample, tissue sample, cells, bacteria, histology section, or buccal swab, either fresh, fixed, frozen, or embedded in paraffin.

As used herein, the term "polynucleotide" includes nucleotides of any number. A polynucleotide includes a nucleic acid molecule of any number of nucleotides including single-stranded RNA, DNA or complements thereof, double-stranded DNA or RNA, and the like. Preferred polynucleotides include SEQ ID NO: 1 or 2 and complements and fragments thereof. The term "oligonucleotide" as used herein includes a polynucleotide molecule comprising any number of nucleotides, preferably, less than about 200 nucleotides. More preferably, oligonucleotides are between 5 and 100 nucleotides in length. Most preferably, oligonucleotides are 10 to 50 nucleotides in length. The exact length of a particular oligonucleotide, however, will depend on many factors, which in turn depend on the ultimate function or use of the oligonucleotide. Short primer molecules generally require lower temperatures to form sufficiently stable hybrid complexes with the template. Preferred oligonucleotides of the present invention include:

5'-GCTCATCATCCCTTTCTCGCT-3' (SEQ ID NO: 13);

5'-AAAGCCCCACCATGGTCGGGT-3' (SEQ ID NO: 14);

5'-CTGATCGCCAAACGAGCAAC-3' (SEQ ID NO: 15);

5'-AAAAACGCCAATGACCACAG-3' (SEQ ID NO: 16)

5'-TGTAAAACGACGGCCAGT-3' (SEQ ID NO: 17); and

5'-CAGGAAACAGCTATGACC-3' (SEQ ID NO: 18);

5'-AGAAGGAGGGTGTTTGTGGGG-3' (SEQ ID NO: 19);

5'-ACCTATAGCACCCACGCCCCT-3' (SEQ ID NO: 20);

5'-GGCCGACGCTCTTGTCTAGCC-3' (SEQ ID NO: 21);

5'-CAAGGGGTTCCTAAGATGAG-3' (SEQ ID NO: 22); and complementary sequences thereof.

Oligonucleotides, such as primer oligonucleotides are preferably single stranded, but may alternatively be double stranded. If double stranded, the oligonucleotide is generally first treated to separate its strands before being used for hybridization purposes or being used to prepare extension products. Preferably, the oligonucleotide is an oligodeoxyribonucleotide. Oligonucleotides may be synthesized chemically by any suitable means known in the art or derived from a biological sample, as for example, by restriction digestion. The source of the oligonucleotides is not essential to the present invention. Oligonucleotides may be labeled, according to any technique known in the art, such as with radiolabels, fluorescent labels, enzymatic labels, proteins, haptens, antibodies, sequence tags, mass tags, fluorescent polarization etc. The term "nucleotide" or nucleic acid as used herein is intended to refer to ribonucleotides, deoxyribonucleotides, acylic derivatives of nucleotides, and functional equivalents thereof, of any phosphorylation state. Functional equivalents of nucleotides are those that act as substrates for a polymerase as, for example, in an amplification method. Functional equivalents of nucleotides are also those that may be formed into a polynucleotide that retains the ability to hybridize in a sequence specific manner to a target polynucleotide.

Such oligonucleotides may be used as probes of a nucleic acid sample, such as genomic DNA, mRNA, or other suitable sources of nucleic acid. For such purposes, the oligonucleotides must be capable of specifically hybridizing to a target polynucleotide or DNA nucleic acid molecule. As used herein, two nucleic acid molecules are said to be capable of specifically hybridizing to one another if the two molecules are capable of forming an anti-parallel, double-stranded nucleic acid structure under hybridizing conditions, whereas they are substantially unable to form a double-stranded structure when incubated with a non-alpha-2BAR nucleic acid molecule under the same conditions. A nucleic acid molecule is said to be the "complement" of another nucleic acid molecule if it exhibits complete complementarity. As used herein, molecules are said to exhibit "complete complementarity" when every nucleotide of one of the molecules is complementary to a nucleotide of the other. Two molecules are said to be "substantially complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described, for example, by Sambrook, J., et al., in *Molecular Cloning, a Laboratory Manual,* 2nd Edition, Cold Spring Harbor Press, Cold Spring Harbor, N.Y. (1989), and by Haymes, B. D., et al. in *Nucleic Acid Hybridization, A Practical Approach*, IRL Press, Washington, D.C. (1985), both herein incorporated by reference). Departures from complete complementarity are therefore permissible, as long as such departures do not completely preclude the capacity of the molecules to form a double-stranded structure.

For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith for the purposes employed. However, for detection purposes particularly using labeled sequence-specific probes, the primers typically have exact complementarity to obtain the best results. Thus, for an oligonucleotide to serve as an allele-specific oligonucleotide, it must generally be complementary in sequence and be able to form a stable double-stranded structure with a target polynucleotide under the particular environmental conditions employed.

The term “allele-specific oligonucleotide” refers to an oligonucleotide that is able to hybridize to a region of a target polynucleotide spanning the sequence, mutation, or polymorphism being detected and is substantially unable to hybridize to a corresponding region of a target polynucleotide that either does not contain the sequence, mutation, or polymorphism being detected or contains an altered sequence, mutation, or polymorphism. As will be appreciated by those in the art, allele-specific is not meant to denote an absolute condition. Allele-specificity will depend upon a variety of environmental conditions, including salt and formamide concentrations, hybridization and washing conditions and stringency. Depending on the sequences being analyzed, one or more allele-specific oligonucleotides may be employed for each target polynucleotide. Preferably, allele-specific oligonucleotides will be completely complementary to the target polynucleotide. However, departures from complete complementarity are permissible. In order for an oligonucleotide to serve as a primer oligonucleotide, however, it typically need only be sufficiently complementary in sequence to be able to form a stable double-stranded structure under the particular environmental conditions employed. Establishing environmental conditions typically involves selection of solvent and salt concentration, incubation temperatures, and incubation times. The terms “primer” or “primer oligonucleotide” as used herein refer to an oligonucleotide as defined herein, which is capable of acting as a point of initiation of synthesis when placed under conditions in which synthesis of a primer extension product which is complementary to a nucleic acid strand is induced, as for example, in a PCR reaction. As with non-primer oligonucleotides, primer oligonucleotides may be labeled, according to any technique known in the art, such as with radiolabels, fluorescent labels, enzymatic labels, proteins, haptens, antibodies, sequence tags, and the like.

In performing the methods of the present invention, the oligonucleotides or the target polynucleotide may be either in solution or affixed to a solid support. Generally, allele-specific oligonucleotides will be attached to a solid support, though in certain embodiments of the present invention allele-specific oligonucleotides may be in solution. In some such embodiments, the target polynucleotide is preferably bound to a solid support. In those embodiments where the allele-specific oligonucleotides or the target polynucleotides are attached to a solid support, attachment may be either covalent or non-covalent. Attachment may be mediated, for example, by antibody-antigen-type interactions, poly-L-Lys, streptavidin or avidin-biotin, salt-bridges, hydrophobic interactions, chemical linkages, LTV cross-ag, baking, and the like. In addition, allele-specific oligonucleotides can be synthesized directly on a solid support or attached to the solid support subsequent to synthesis. In a preferred embodiment, allele-specific oligonucleotides are affixed on a solid support such that a free 3'-OH is available for polymerase-mediated primer extension.

Suitable solid supports for the present invention include substrates constructed of silicon, glass, plastic (polystyrene, nylon, polypropylene, etc.), paper, etc. Solid supports may be formed, for example, into wells (as in 96-well dishes), plates, slides, sheets, membranes, fibers, chips, dishes, and beads. In certain embodiments of the present invention, the solid support is treated, coated, or derivatized so as to facilitate the immobilization of an allele-specific oligonucleotide or a target polynucleotide. Preferred treatments include coating, treating, or derivatizing with poly-L-Lys, streptavidin, antibodies, silane derivatives, low salt, or acid.

Providing Alpha-2B Adrenergic Receptor Molecules

The alpha-2B-adrenergic receptor molecule (amino acids) identified as SEQ ID NO: 7 or 8 or fragments thereof and DNA encoding the alpha-2B-adrenergic receptor molecule (SEQ ID NO: 1 or 2), fragments or compliments of the nucleic acids can be obtained from the sample. These molecules may also be chemically synthesized by methods known in the art. Suitable methods for synthesizing the protein are described by Stuart and Young in *Solid Phase Peptide Synthesis*, Second Edition, Pierce Chemical Company (1984), *Solid Phase Peptide Synthesis, Methods Enzymol.,* 289, Academic Press, Inc, New York (1997). Suitable methods for synthesizing DNA are described by Caruthers in *Science* 230:281–285 (1985) and “DNA Structure, Part A: Synthesis and Physical Analysis of DNA,” Lilley, D. M. J. and Dahlberg, J. E. (Eds.), *Methods Enzymol.,* 211, Academic Press, Inc., New York (1992).

Accordingly, the nucleic acids, probes and primers of the present invention can be synthesized chemically from the nucleotides in whole or in part by methods known in the art. Such methods include those described by Caruthers in *Science* 230:281–285 (1985) and “DNA Structure, Part A: Synthesis and Physical Analysis of DNA,” Lilley, D. M. J. and Dahlberg, J. E. (Eds.), *Methods Enzymol.,* 211, Academic Press, Inc., New York (1992).

DNA may also be synthesized by preparing overlapping double-stranded oligonucleotides, filling in the gaps, and ligating the ends together. The DNA may be cloned in a suitable recombinant host cell and expressed. The DNA and protein may be recovered from the host cell. See, generally, Sambrook, J. et al. (Eds.), *Molecular Cloning*, Second Edition, Cold Spring Harbor Laboratory Press, Cold Spring Harbor, N.Y. (1989) and Ausubel, F. M. et al. (Eds.), *Current Protocols in Molecular Biology*, John Wiley & Sons, Inc., New York (1999).

The nucleic acid molecules or DNA encoding the alpha-2B adrenergic receptor molecule identified as SEQ ID NO: 1 or 2 of the invention may be replicated and used to express recombinant protein following insertion into a wide variety of host cells in a wide variety of cloning and expression vectors. The host may be prokaryotic or eukaryotic. The DNA may be obtained from natural sources and, optionally, modified. The genes may also be synthesized in whole or in part.

Cloning vectors may comprise segments of chromosomal, non-chromosomal and synthetic DNA sequences. Some suitable prokaryotic cloning vectors include plasmids from *E. coli*, such as colE1, pCR1, pBR322, pMB9, pUC, pKSM, and RP4. Prokaryotic vectors also include derivatives of phage DNA such as M13 and other filamentous single-stranded DNA phages.

Vectors for expressing proteins in bacteria, especially *E. coli*, are also known. Such vectors include the pK233 (or any of the tac family of plasmids), T7, pBluescript II, bacteriophage lamba ZAP, and lambda $P_L$ (Wu, R. (Ed.), *Recombinant DNA Methodology II, Methods Enzymol.*, Academic Press, Inc., New York, (1995)). Examples of vectors that express fusion proteins are PATH vectors described by Dieckmann and Tzagoloff in *J. Biol. Chem.* 260, 1513–1520 (1985). These vectors contain DNA sequences that encode anthranilate synthetase (TrpE) followed by a polylinker at the carboxy terminus. Other expression vector systems are based on beta-galactosidase (pEX); maltose binding protein (pMAL); glutathione S-transferase (pGST or PGEX)—see Smith, D. B. *Methods Mol. Cell. Biol.* 4:220–229 (1993); Smith, D. B. and Johnson, K. S., Gene 67:31–40 (1988); and *Peptide Res.* 3:167 (1990), and TRX (thioredoxin) fusion protein (TRXFUS)—see LaVallie, R. et al., *Bio/Technology* 11:187–193 (1993). A particularly preferred plasmid of the present invention is pBC12BI.

Vectors useful for cloning and expression in yeast are available. Suitable examples are 2 μm circle plasmid, Ycp50, Yep24, Yrp7, Yip5, and pYAC3 (Ausubel, F. M. et al. (Eds.), *Current Protocols in Molecular Biology*, John Wiley & Sons, Inc., New York, (1999)).

Suitable cloning/expression vectors for use in mammalian cells are also known. Such vectors include well-known derivatives of SV-40, adenovirus, cytomegalovirus (CMV) retrovirus-derived DNA sequences. Any such vectors, when coupled with vectors derived from a combination of plasmids and phage DNA, i.e. shuttle vectors, allow for the isolation and identification of protein coding sequences in prokaryotes.

Further eukaryotic expression vectors are known in the art (e.g., P. J. Southern and P. Berg, *J. Mol. Appl. Genet.* 1:327–341 (1982); S. Subramani et al., *Mol. Cell. Biol.* 1:854–864 (1981); R. J. Kaufmann and P. A. Sharp, "Amplification And Expression Of Sequences Cotransfected with A Modular Dihydrofolate Reductase Complementary DNA Gene," *J. Mol. Biol.* 159:601–621 (1982); R. J. Kaufmann and P. A. Sharp, *Mol. Cell. Biol.* 159:601–664 (1982); S. I. Scahill et al, "Expression And Characterization Of The Product Of A Human Immune Interferon DNA Gene In Chinese Hamster Ovary Cells," *Proc. Natl. Acad. Sci. USA* 80:4654–4659 (1983); G. Urlaub and L. A. Chasin, *Proc. Natl. Acad. Sci. USA* 77:4216–4220 (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, the tet system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Useful expression hosts include well-known prokaryotic and eukaryotic cells. Some suitable prokaryotic hosts include, for example, *E. coli*, such as *E. coli* SG-936, *E. coli* HB 101, *E. coli* W3110, *E. coli* X1776, *E. coli* X2282, *E. coli* DH1, *E. coli* DH5alphaF, and *E. coli* MRC1, *Pseudomonas, Bacillus*, such as *Bacillus subtilis*, and *Streptomyces*. Suitable eukaryotic cells include yeasts and other fungi, insect, animal cells, such as COS cells and CHO cells, human cells and plant cells in tissue culture. A particularly preferred host cell is CHO.

The alpha-2B adrenergic receptor molecule identified as SEQ ID NO: 7 or 8 can be the entire protein as it exists in nature isolated from the sample, or an antigenic, preferably immunogenic, fragment of the whole protein. Antigenic and/or immunogenic fragments of antigenic and/or immunogenic proteins may be identified by methods known in the art.

Fragments containing antigenic sequences may be selected on the basis of generally accepted criteria of potential antigenicity and/or exposure. Such criteria include the hydrophilicity and relative antigenic index, as determined by surface exposure analysis of proteins. The determination of appropriate criteria is known to those skilled in the art, and has been described, for example, by Hopp, T., Methods Enzymol., 178:571–585 Academic Press, Inc., New York (1989); Becker, Y., Virus Genes 6:79–93 (1992); Regenmortel, V and Pellequer, J. L., Pept. Res. 7:224–228 (1994); Gallet, X. et al., Prot. Eng. 8:829–834 (1995); Kyte et al., J. Mol. Biol. 157:105–132 (1982); Emini, E. A. et al., J. Virol. 55:836–839 (1985); Jameson et al., CA BIOS 4:181–186 (1988); and Karplus et al., Naturwissenschaften 72:212–213 (1985). Amino acid domains predicted by these criteria to be surface exposed are selected preferentially over domains predicted to be more hydrophobic or hidden.

Methods for isolating and identifying antigenic fragments from known antigenic proteins are described by Salfeld et al. in J. Virol. 63:798–808 (1989) and by Isola et al. in J. Virol. 63:2325–2334 (1989). An alternative means for identifying antigenic sites on protein is by the use of synthetic peptide combinatorial library or phage-display peptide library as described in Combinatorial Peptide Library Protocols, Cabilly, S. (Ed.), Humana Press, New York, 1998; Pinilla, C. et al., Pept. Res. 8:250–257 (1995); Scala, G. et al., J. Immunol. 162:6155–6161 (1999); Pereboeva, L. A. et al., J. Med. Virol. 56:105–111 (1998); and Demkowicz, W. E. et al., J. Virol. 66:386–398 (1992).

The alpha-2B adrenergic receptor molecule is isolated from the sample by standard methods known in the art. Some suitable methods include precipitation and liquid/chromatographic protocols such as ion exchange, hydrophobic interaction and gel filtration See, for example, Guide to Protein Purification, Deutscher, M. P. (Ed.) Methods Enzymol., 182, Academic Press, Inc., New York (1990) and Scopes, R. K. and Cantor, C. R. (Eds.), Protein Purification (3d), Springer-Verlag, New York (1994).

Alternatively, purified material is obtained by separating the protein on preparative SDS-PAGE gels, slicing out the band of interest and electroeluting the protein from the polyacrylamide matrix by methods known in the art. The detergent SDS is removed from the protein by known methods, such as by dialysis or the use of a suitable column, such as the Extracti-Gel column from Pierce.

Detection of Polymorphisms

The polymorphisms of the present invention may be detected directly or indirectly using any of a variety of suitable methods. Suitable methods comprise direct or indirect sequencing methods, restriction site analysis, hybridization methods, nucleic acid amplification methods, gel migration methods, the use of antibodies that are specific for the proteins encoded by the different alleles of the polymorphism, or by other suitable means. Alternatively, many such methods are well known in the art and are described, for example in T. Maniatis et al., *Molecular Cloning, a Laboratory Manual, 2nd Edition*, Cold Spring Harbor Press, Cold Spring Harbor, N.Y. (1989), J. W. Zyskind et al., *Recombinant DNA Laboratory Manual*, Academic Press, Inc., New York (1988), and in R. Elles, *Molecular Diagnosis of Genetic Diseases*, Humana Press, Totowa, N.J. (1996), each herein incorporated by reference.

Exemplary antibody molecules for detecting the alpha-2BAR amino acid variants are intact immunoglobulin molecules, substantially intact immunoglobulin molecules, or those portions of immunoglobulin molecules that contain the antigen binding site. Polyclonal or monoclonal antibodies may be produced by methods conventionally known in the art (e.g., Kohler and Milstein, Nature, 256:495–497 (1975); Campbell "*Monoclonal Antibody Technology, the Production and Characterization of Rodent and Human Hybridomas",* 1985, In: "*Laboratory Techniques in Biochemistry and Molecular Biology*," Eds. Burdon et al., Volume 13, Elsevier Science Publishers, Amsterdam). The antibodies or antigen binding fragments thereof may also be produced by genetic engineering. The technology for expression of both heavy and light chain genes in *E. coli* is described in Huse et al., 1989*, Science* 246:1275–1281. The antibodies may also be humanized (e.g., Queen, C. et al. 1989 *Proc. Natl. Acad. Sci.* 86; 10029).

Identification methods may be of either a positive-type or a negative-type. Positive-type methods determine the identity of a nucleotide contained in a polymorphic site, whereas negative-type methods determine the identity of a nucleotide not present in a polymorphic site. Thus, a wild-type site may be identified either as wild-type or not mutant. For example, at a biallelic polymorphic site where the wild-type allele contains a cytosine and the mutant allele contains adenine, a site may be positively determined to be either adenine or cytosine or negatively determined to be not adenine (and thus cytosine) or not cytosine (and thus adenine).

Alternately, if the polymorphism is a deletion, or addition then the complementary sequence can be detected. As another example, in hybridization-based assay, a target polynucleotide containing a mutated site may be identified positively by hybridizing to an allele-specific oligonucleotide containing the mutated site or negatively, by failing to hybridize to a wild-type allele-specific oligonucleotide. Similarly, a restriction site may be determined to be present or lacking.

Direct Sequencing

Direct sequencing by methods such as dideoxynucleotide sequencing (Sanger), cycle sequencing, or Maxam-Gilbert sequencing are examples of suitable methods for determining the identity of a nucleotide at a polymorphic site of a target polynucleotide. Such methods are widely known in the art and are discussed at length, in the above-cited texts.

Both the dideoxy-mediated method and the Maxam-Gilbert method of DNA sequencing require the prior isolation of the DNA molecule which is to be sequenced. The sequence information is obtained by subjecting the reaction products to electrophoretic analysis (typically using polyacrylamide gels). Thus, a sample is applied to a lane of a gel, and the various species of nested fragments are separated from one another by their migration velocity through the gel. The number of nested fragments which can be separated in a single lane is approximately 200–300 regardless of whether the Sanger or the Maxam-Gilbert method is used. Thus, in order to identify a nucleotide at a particular polymorphic site in a target polynucleotide, extraneous sequence information is typically produced. The chief advantage of direct sequencing lies in its utility for locating previously unidentified polymorphic sites.

One of the problems that has encumbered the development of useful assays for genetic polymorphisms is that in many cases, it is desirable to determine the identity of multiple polymorphic loci. This frequently requires sequencing significant regions of the genome or performing multiple assays with an individual patient sample.

Restriction Site Analysis

Restriction enzymes are specific for a particular nucleotide sequence. In certain embodiments of the present invention, the identity of a nucleotide at a polymorphic site is determined by the presence or absence of a restriction enzyme site. A large number of restriction enzymes are known in the art and, taken together, they are capable of recognizing at least one allele of many polymorphisms.

This feature of restriction enzymes may be utilized in a variety of methods for identifying a polymorphic site. Restriction fragment length polymorphism (RFLP) analysis is an example of a suitable method for identifying a polymorphic site with restriction enzymes (Lentes et al., *Nucleic Acids Res.* 16:2359 (1988); and C. K. McQuitty et al., *Hum. Genet.* 93:225 (1994)). In RFLP analysis, at least one target polynucleotide is digested with at least one restriction enzyme and the resultant "restriction fragments" are separated based on mobility in a gel. Typically, smaller fragments migrate faster than larger fragments. Consequently, a target polynucleotide that contains a particular restriction enzyme recognition site will be digested into two or more smaller fragments, which will migrate faster than a larger fragment lacking the restriction enzyme site. Knowledge of the nucleotide sequence of the target polynucleotide, the nature of the polymorphic site, and knowledge of restriction enzyme recognition sequences guide the design of such assays.

Hybridization

Several suitable hybridization-based methods for identifying a nucleotide at a polymorphic site have been described. Generally, allele-specific oligonucleotides are utilized in performing such hybridization-based methods. Preferably, allele-specific oligonucleotides are chosen that are capable of specifically hybridizing to only one allele of an alpha-2B molecule at a region comprising a polymorphic site. In those embodiments wherein more than one polymorphic site is identified, sets of allele-specific oligonucleotides are preferably chosen that have melting temperatures within 5° C. of each other when hybridizing to their complete complement. Most preferably, such sets of allele-specific oligonucleotides are chosen so as to have melting temperatures within 20° C. of each other. Examples of suitable hybridization methods are described in standard manuals such as Molecular Cloning, A Laboratory Manual (2nd Ed., Sambrook, Fritsch and Maniatis, Cold Spring Harbor); and Current Protocols in Molecular Biology (Eds. Ausubel, Brent, Kingston, More, Feidman, Smith and Stuhl, Greene Publ. Assoc., Wiley-Interscience, NY, N.Y., 1992) or that are otherwise known in the art. Examples of preferred hybridization methods include Southern, northern, and dot blot hybridizations, allele-specific oligonucleotide hybridizations (Hall et al., *The Lancet* 345:1213–1214 (1995)), reverse dot blot hybridizations (Sakai et al., *Nucl. Acids. Res.* 86:6230–6234 (1989)), DNA chip hybridizations (Drmanac et al., U.S. Pat. No. 5,202,231), and hybridizations to allele-specific oligonucleotides.

Macevicz (U.S. Pat. No. 5,002,867), for example, describes a method for deriving nucleic acid sequence information via hybridization with multiple mixtures of oligonucleotide probes. In accordance with such method, the sequence of a target polynucleotide is determined by permitting the target to sequentially hybridize with sets of probes having an invariant nucleotide at one position, and variant nucleotides at other positions. The Macevicz method determines the nucleotide sequence of the target by hybridizing the target with a set of probes, and then determining the number of sites that at least one member of the set is capable of hybridizing to the target (i.e. the number of "matches"). This procedure is repeated until each member of a sets of probes has been tested.

Polymerase-Mediated Primer Extension

The "Genetic Bit Analysis" ("GBA") method disclosed by Goelet, P. et al. (WO92/15712, and U.S. Pat. Nos. 5,888,819 and 6,004,744, all herein incorporated by reference), is a preferred method for determining the identity of a nucleotide at a predetermined polymorphic site in a target polynucleotide. The target polynucleotide can be, for example, nucleic acids encoding the alpha-2B adrenergic receptor molecule or complements or fragments thereof. GBA is a method of polymorphic site interrogation in which the nucleotide sequence information surrounding a polymorphic site in a target nucleic acid sequence is used to design an oligonucleotide primer that is complementary to a region immediately adjacent to at the 3' or 5' end of the target polynucleotide, but not including, the variable nucleotide(s) in the polymorphic site of the target polynucleotide. The target polynucleotide is isolated from the biological sample and hybridized to the interrogating primer. In some embodiments of the present invention, following isolation, the target polynucleotide may amplified by any suitable means prior to hybridization to the interrogating primer. The primer is extended by a single labeled terminator nucleotide, such as a dideoxynucleotide, using a polymerase, often in the presence of one or more chain terminating nucleoside triphosphate- precursors (or suitable, analogs). A detectable signal is thereby produced.

For example, to detect the polymorphic site on target nucleic acids encoding the alpha-2BAR, a primer oligonucleotide complementary to a region of SEQ ID NO:1 can be hybridized at the primer's 3' end to a region up to and including, for example, nucleotide position number 902 of SEQ ID NO:1. If the primer is extended at its 3' end by a single labeled terminator nucleotide, such as for example the dideoxynucleotide ddTTP, using a polymerase, a detectable signal is produced indicating the complementary nucleotide A at nucleotide position 903. This indicates the wild-type alpha-2BAR and thus the polymorphic alpha-2BAR is identified.

To detect the polymorphic site on target nucleic acids encoding the alpha-2BAR, a primer oligonucleotide complementary to a region of SEQ ID NO: 2 can be hybridized at the primer's 3' end to a region up to and including, for example, nucleotide position number 902 of SEQ ID NO: 2. If the primer is extended at its 3' end by a single labeled terminator nucleotide, such as for example the dideoxynucleotide ddCTP, using a polymerase, a detectable signal is produced indicating the complementary nucleotide G at nucleotide position 903. This indicates the mutant alpha-2BAR shown and thus the polymorphic alpha-2BAR is identified.

In some embodiments of the present invention, the oligonucleotide is bound to a solid support prior to the extension reaction. In other embodiments, the extension reaction is performed in solution and the extended product is subsequently bound to a solid support.

In an alternate sub-embodiment of GBA, the primer is detectably labeled and the extended terminator nucleotide is modified so as to enable the extended primer product to be bound to a solid support. An example of this would be where the primer is fluorescently labeled and the terminator nucleotide is a biotin-labeled terminator nucleotide and the solid support is coated or derivatized with avidin or streptavidin. In such embodiments, an extended primer would thus be enabled to bind to a solid support and non-extended primers would be unable to bind to the support, thereby producing a detectable signal dependent upon an a successful extension reaction.

Ligase/polymerase mediated genetic bit analysis (U.S. Pat. Nos. 5,679,524, and 5,952,174, both herein incorporated by reference) is another example of a suitable polymerase mediated primer extension method for determining the identity of a nucleotide at a polymorphic site. Ligase/polymerase GBA utilizes two primers. Generally, one primer is detectably labeled, while the other is designed to be affixed to a solid support. In alternate embodiments of ligase/polymerase GBA, extended nucleotide is detectably labeled. The primers in ligase/polymerase GBA are designed to hybridize to each side of a polymorphic site, such that there is a gap comprising the polymorphic site. Only a successful extension reaction, followed by a successful ligation reaction enables the production of the detectable signal. The method offers the advantages of producing a signal with considerably lower background than is possible by methods employing only hybridization or primer extension alone.

The present invention includes an alternate method for determining the identity of a nucleotide at a predetermined polymorphic site in a target polynucleotide. This method is described in Soderlund et al., U.S. Pat. No. 6,013,431, the entire disclosure is herein incorporated by reference. In this alternate method, the polymorphic site is interrogated where nucleotide sequence information surrounding a polymorphic site in a target nucleic acid sequence is used to design an oligonucleotide primer that is complementary to a region flanking the 3' or 5' end of the target polynucleotide, but not including, the variable nucleotide(s) in the polymorphic site of the target polynucleotide. The target polynucleotide is isolated from the biological sample and hybridized to the interrogating primer. In some embodiments of this method, following isolation, the target polynucleotide may be amplified by any suitable means prior to hybridization to the interrogating primer. The primer is extended, using a polymerase, often in the presence of a mixture of at least one labeled deoxynucleotide and one or more chain terminating nucleoside triphosphate- precursors (or suitable, analogs). A detectable signal is thereby produced upon incorporation of the labeled deoxynucleotide into the primer.

Cohen, D. et al. (PCT Application WO91/02087) describes another example of a suitable method for determining the identity of a polymorphic site, wherein dideoxynucleotides are used to extend a single primer by a single nucleotide in order to determine the sequence at a desired locus. Ritterband, M., et al., (PCT Application WO95/17676) describes an apparatus for the separation, concentration and detection of such target molecules in a liquid sample. Cheeseman, P.C. (U.S. Pat. No. 5,302,509) describes a related method of determining the sequence of a single stranded DNA molecule. The method of Cheeseman employs fluorescently labeled 3'-blocked nucleotide triphosphates with each base having a different fluorescent label.

Wallace et al. (PCT Application WO89/10414) describes multiple PCR procedures which can be used to simultaneously amplify multiple regions of a target by using allele specific primers. By using allele specific primers, amplification can only occur if a particular allele is present in a sample.

Several other suitable primer-guided nucleotide incorporation procedures for assaying polymorphic sites in DNA have been described (Komher, J. S. et al., *Nucl. Acids. Res.* 17:7779–7784 (1989); Sokolov, B. P., *Nucl. Acids Res.* 18:3671 (1990); Syvdnen, A.-C., et al., *Genomics* 8:684–692 (1990); Kuppuswamy, M. N. et al., *Proc. Natl. Acad. Sci.* (*U.S.A.*) 88:1143–1147 (1991); Bajaj et al. (U.S. Pat. No. 5,846,710); Prezant, T. R. et al., *Hum. Mutat.* 1:159–164 (1992); Ugozzoli, L. et al., *GATA* 9:107–112 (1992); Nyrén, P. et al., *Anal. Biochem.* 208:171–175 (1993)). These methods differ from GBA in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide will result in signals that are proportional to the length of the run (Syvdnen, A.-C., et al., *Amer. J. Hum. Genet.* 52:46–59 (1993)). Such a range of locus-specific signals could be more complex to interpret, especially for heterozygotes, compared to the simple, ternary (2: 0, 1: 1, or 0: 2) class of signals produced by the GBA method.

Amplification

In certain embodiments of the present invention, the detection of polymorphic sites in a target polynucleotide may be facilitated through the use of nucleic acid amplification methods. Such methods may be used to specifically increase the concentration of the target polynucleotide (i.e., sequences that span the polymorphic site, or include that site and sequences located either distal or proximal to it). Such amplified molecules can be readily detected by gel electrophoresis, or other means.

The most preferred method of achieving such amplification employs PCR (e.g., Mullis, et al., U.S. Pat. No. 4,965, 188), using primer pairs that are capable of hybridizing to the proximal sequences that define or flank a polymorphic site in its double-stranded form.

In some embodiments of the present invention, the amplification method is itself a method for determining the identity of a polymorphic site, as for example, in allele-specific PCR (J. Turki et al., *J. Clin. Invest.* 95:1635–1641 (1995)). In allele-specific PCR, primer pairs are chosen such that amplification is dependent upon the input template nucleic acid containing the polymorphism of interest. In such embodiments, primer pairs are chosen such that at least one primer is an allele-specific oligonucleotide primer. In some sub-embodiments of the present invention, allele-specific primers are chosen so that amplification creates a restriction site, facilitating identification of a polymorphic site. In other embodiments of the present invention, amplification of the target polynucleotide is by multiplex PCR (Wallace et al. (PCT Application WO89/10414)). Through the use of multiplex PCR, a multiplicity of regions of a target polynucleotide may be amplified simultaneously. This is particularly advantageous in those embodiments wherein greater than a single polymorphism is detected.

In lieu of PCR, alternative methods, such as the "Ligase Chain Reaction" ("LCR") may be used (Barany, F., *Proc. Natl. Acad. Sci.* (*U.S.A.*) 88:189–193 (1991)). LCR uses two pairs of oligonucleotide probes to exponentially amplify a specific target. The sequences of each pair of oligonucleotides is selected to permit the pair to hybridize to abutting sequences of the same strand of the target. Such hybridization forms a substrate for a template-dependent ligase. As with PCR, the resultant product serves as a template in subsequent amplification cycles, resulting in an exponential amplification of the desired sequence.

In accordance with the present invention, LCR can be performed using oligonucleotides having sequences derived from the same strand, located proximal and distal to the polymorphic site. In one embodiment, either oligonucleotide is designed so as to include the actual polymorphic site of the polymorphism. In such an embodiment, the reaction conditions are selected such that the oligonucleotides can be ligated together only if the target molecule contains the specific nucleotide in the polymorphic site that is complementary to the polymorphic site present on the oligonucleotide. In an alternative embodiment, the oligonucleotides will not include the polymorphic site, such that when they hybridize to the target molecule, a "gap" of at least one nucleotide is created (see, Segev, D., PCT Application WO90/01069 and U.S. Pat. No. 6,004,826). This gap is then "filled" with complementary dNTPs (as mediated by DNA polymerase), or by an additional pair of oligonucleotides. Thus, at the end of each cycle, each single strand has a complement capable of serving as a target during the next cycle and exponential amplification of the desired sequence is obtained.

The "Oligonucleotide Ligation Assay" ("OLA") (Landegren, U. et al., *Science* 241:1077–1080 (1988)) shares certain similarities with LCR and is also a suitable method for analysis of polymorphisms. The OLA protocol uses two oligonucleotides, which are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Nickerson, D. A. et al. have described a nucleic acid detection assay that combines attributes of PCR and OLA (Nickerson, D. A. et al., *Proc. Natl. Acad. Sci.* (*U.S.A.*) 87:8923–8927 (1990)). In this method, PCR is used to achieve the exponential amplification of target DNA, which is then detected using OLA.

Schemes based on ligation of two (or more) oligonucleotides in the presence of nucleic acid having the sequence of the resulting "dioligonucleotide", thereby amplifying the dioligonucleotide, are known (Wu, D. Y. et al., *Genomics* 4:560 (1989); Adams, C., WO94/03630), and are also suitable methods for the purposes of the present invention.

One convenient method for identifying genetic polymorphisms is called random amplified polymorphic DNA ("RAPD"). It requires no probe DNA and no advance information about the genome of the organism, but uses a set of PCR primers of 8 to 10 bases whose sequence is random. The random primers are tried singly or in pairs in PCR reactions, and since the primers are short, they often anneal to the target DNA at multiple sites. Some primers anneal in the proper orientation and at a suitable distance from each other to support amplification of the unknown sequence between them. Among the set of fragments are ones that can be amplified from some genomic DNA samples but not from others, which means that the presence or absence of the fragment is polymorphic in the population of organisms. An important feature of RAPDs and other detection methods based on PCR amplification is that presence of the fragment is dominant to absence of the fragment. Thus, if one allele (+) supports amplification but the alternative allele (−) does not, then DNA from the genotypes +/+ and +/− will support amplification equally well, whereas DNA from the genotype −/− will not support amplification. The +allele is therefore dominant to the −allele in regard to the corresponding RAPD fragment.

Other known nucleic acid amplification procedures include transcription-based amplification systems (Malek, L. T. et al., U.S. Pat. No. 5,130,238; Davey, C. et al., European Patent Application 329,822; Schuster et al., U.S. Pat. No. 5,169,766; Miller, H. I. et al., PCT-Application WO89/06700; Kwoh, D. et al., *Proc. Natl. Acad. Sci.* (*U.S.A.*) 86:1173 Z1989); Gingeras, T. R. et al., PCT Application WO88/10315)), or isothermal amplification methods (Walker, G. T. et al., *Proc. Natl. Acad. Sci.* (*U.S.A.*) 89:392–396 (1992)) may also be used.

Gel Migration

Single strand conformational polymorphism (SSCP; M. Orita et al., *Genomics* 5:874–879 (1989); Humphfies et al., *In: Molecular Diagnosis of Genetic Diseases*, R. Elles, ed. pp 321–340 (1996)) and temperature gradient gel electrophoresis (TGGE; R. M. Wartell et al., *Nucl. Acids Res.* 18:2699–2706 (1990)) are examples of suitable gel migration-based methods for determining the identity of a polymorphic site. In SSCP, a single strand of DNA will adopt a conformation that is uniquely dependent of its sequence composition. This conformation is usually different, if even a single base is changed. Thus, certain embodiments of the present invention, SSCP may be utilized to identify polymorphic sites, as wherein amplified products (or restriction fragments thereof) of the target polynucleotide are denatured, then run on a non-denaturing gel. Alterations in the mobility of the resultant products is thus indicative of a base change. Suitable controls and knowledge of the "normal" migration patterns of the wild-type alleles may be used to identify polymorphic variants.

Temperature gradient gel electrophoresis (TGGE) is a related procedure, except that the nucleic acid sample is run on a denaturing gel. In embodiments of the present invention utilizing TGGE to identify a polymorphic site, the amplified products (typically PCR products) are electrophoresed over denaturing polyacrylamide gel, wherein the temperature gradient is optimized for separation of the target polynucleotide segments (E. Reihsaus et al., *Am. J. Respir. Cell Mol. Biol.* 8:334–339 (1993), herein incorporated by reference). This method is able to detect single base changes in the target polynucleotide sequence.

Kits of the Present Invention

The present invention provides diagnostic and therapeutic kits that include at least one primer for detecting at least one polymorphism in nucleic acids encoding an alpha-2B adrenergic receptor molecule. Preferably, the kit includes a container having an oligonucleotide comprising a region of SEQ ID NOs: 1 or 2 or complement thereof for detecting the polymorphism as described. In one embodiment, the kit includes primers for amplifying regions of nucleic acids encoding the alpha-2B adrenergic receptor molecule where at least one of the polymorphisms is found, such as for example SEQ ID NOs: 1 or 2. In an alternate embodiment, the kit includes allele-specific oligonucleotides, specific for both mutant and wild-type alleles of at least one polymorphism. The kit may also contain sources of "control" target polynucleotides, as positive and negative controls. Such sources may be in the form of patient nucleic acid samples, cloned target polynucleotides, plasmids or bacterial strains carrying positive and negative control DNA. Kits according to the invention can include one or more containers, as well as additional reagent(s) and/or active and/or inert ingredient(s) for performing any variations on the methods of the invention. Exemplary reagents include, without limitation, one or more primers, one or more terminator nucleotides, such as dideoxynucleotides, that are labeled with a detectable marker. The kits can also include instructions for mixing or combining ingredients or use.

The invention also provides diagnostic and experimental kits which include monospecific antibodies that enable the detection, purification and/or separation alpha-2B adrenergic receptor molecule or fragments thereof in a specific and reproducible manner. In these kits, the antibodies may be provided with means for binding to detectable marker moieties or substrate surfaces. Alternatively, the kits may include the antibodies already bound to marker moieties or substrates. The kits may further include positive and/or negative control reagents as well as other reagents for adapting the use of the antibodies to particular experimental and/or diagnostic techniques as desired. The kits may be prepared for in vivo or in vitro use, and may be particularly adapted for performance of any of the methods of the invention, such as ELISA. For example, kits containing antibody bound to multi-well microtiter plates can be manufactured.

Genotyping and Haplotyping Methods

The polymorphic sites of the present invention occurring in the polynucleotide encoding alpha-2B adrenergic receptor gene can be detected by any of the above methods and used to determine the genotype. As used herein, the term "genotyping" refers to determining the presence, absence or identity of a polymorphic site in a target nucleic acid (identified as SEQ ID NOs: 1or 2). Preferably, the genotyping is performed on two copies of the alpha-2B-adrenergic receptor gene.

In one embodiment, genotyping involves obtaining a sample containing the target nucleic acid, treating the sample to obtain single stranded nucleic acids, if such nucleic acid is double-stranded, so as to obtain unpaired nucleotide bases spanning the specific position. If the target nucleic acid is single-stranded, this step is not necessary. The sample containing the target nucleic acid is contacted with an oligonucleotide under hybridizing conditions. The oligonucleotide is capable of hybridizing with a stretch of nucleotide bases present in the target nucleic acid, adjacent to the polymorphic site to be identified (e.g., deletion, insertion, mutation, or a single nucleotide polymorphisms), so as to form a duplex between the oligonucleotide and the target nucleic acid. When the oligonucleotide is "immediately adjacent" the polymorphic site to be identified, the oligonucleotide hybridizes with the target nucleic acid in such a way that either the 3' or 5' end of the oligonucleotide is complementary to a nucleotide on the target nucleic acid that is located immediately 5' or 3', respectively, of the polymorphic site to be identified. It is also contemplated herein that the oligonucleotide can be a fragment complementary to SEQ ID NO: 1 or 2, and not immediately adjacent to the polymorphic site to be identified, such that the 3' end of the oligonucleotide is 1 up to 50, preferably 1 up to 10, nucleotides upstream or downstream from the polymorphic site to be identified in the target nucleic acid.

As used herein, upstream includes that part of a strand of DNA or RNA molecule that is towards the 5'end of the polymorphic site or site of interest. For example, upstream of the polymorphic site (nucleotide positions 901 to 909 of SEQ ID NO: 1 or 2) includes nucleotide positions 880 to 900. Downstream includes that part of a strand of DNA or RNA molecule lying towards the 3' end of the polymorphic site or site of interest. For example, downstream of the polymorphic site (nucleotide positions 901 to 909 of SEQ ID NO: 1 or 2) includes nucleotide positions 910 to 930.

In one preferred embodiment of the present invention, to detect the polymorphic site on target nucleic acids encoding the alpha-2BAR, a primer oligonucleotide complementary to a region of SEQ ID NO: 1 can be hybridized at the primer's 3' end to a region up to and including, for example, nucleotide position number 902 of SEQ ID NO: 1. If the primer is extended at its 3' end by a single labeled terminator nucleotide, such as for example the dideoxynucleotide ddTTP, using a polymerase, a detectable signal is produced indicating the complementary nucleotide A at nucleotide position 903. This indicates the wild-type alpha-2BAR and thus the polymorphic alpha-2BAR is identified.

To detect the polymorphic site on target nucleic acids encoding the alpha-2BAR, a primer oligonucleotide complementary to a region of SEQ ID NO: 2 can be hybridized at the primer's 3' end to a region up to and including, for example, nucleotide position number 902 of SEQ ID NO: 2. If the primer is extended at its 3' end by a single labeled terminator nucleotide, such as for example the dideoxynucleotide ddCTP, using a polymerase, a detectable signal is produced indicating the complementary nucleotide G at nucleotide position 903. This indicates the mutant alpha-2BAR and thus the polymorphic alpha-2BAR is identified. The above described methods are useful in determining the alpha-2BAR genotype or haplotype. In one embodiment, the present invention provides a method of genotyping an alpha-2B adrenergic receptor gene comprising: obtaining a sample having a polynucleotide encoding an alpha-2B-adrenergic receptor molecule comprising SEQ ID NOs: 1 or 2 or fragment or complement of the polynucleotide; and detecting in the sample a polymorphic site comprising nucleotide positions 901 to 909 of SEQ ID Nos: 1 or 2 or fragment or complement thereof.

In the most preferred embodiment, the present invention includes methods of genotyping nucleic acids encoding an alpha-2B adrenergic receptor molecule from a sample of an individual which includes isolating from the individual, the sample having a polynucleotide encoding the alpha-2B adrenergic receptor molecule identified as SEQ ID NO: 1 or 2 or fragment or complement thereof; incubating the polynucleotide with at least one oligonucleotide, the oligonucleotide having a nucleotide sequence that is complementary to a region of the polynucleotide, and which, when hybridized to the region permits the identification of the nucleotide present at a polymorphic site of the polynucleotide, wherein the incubation is under conditions sufficient to allow specific hybridization to occur between complementary nucleic acid molecules; permitting the hybridization to occur; and identifying the polymorphic site to obtain the genotype of the individual. A genotype includes a 5' to 3' sequence of nucleotide pair(s) found at one or more polymorphic sites in a locus on a pair of homologous chromosomes in an individual.

The present invention includes a method for haplotyping an alpha-2B adrenergic receptor gene comprising: obtaining a sample having a polynucleotide encoding an alpha-2B-adrenergic receptor molecule comprising SEQ ID NOs: 1 or 2 or fragment or complement of the polynucleotide; detecting in the sample a polymorphic site comprising nucleotide positions 901 to 909 of SEQ ID NOs: 1 or 2 or fragment or complement thereof on one copy of the alpha-2B-adrenergic receptor gene; and determining the identity of an additional polymorphic site on the copy of the alpha-2B-adrenergic receptor gene.

As used herein, haplotyping includes determining the identity of two or more polymorphic sites in a locus on a single chromosome from a single individual. Haplotypes include 5' to 3' sequence of nucleotides found at two or more polymorphic sites in a locus on a single chromosome from an individual. The preferred polymorphic sites are discussed above.

Once the haplotype or genotype is determined in the individual, this information can be compared to any particular alpha-2BAR genotype or haplotype found in a population. In a preferred embodiment, the alpha-2BAR genotype may also comprise the nucleotide pair(s) detected at one or more additional alpha-2BAR polymorphic sites. The population may be a reference population, a family population, a same sex population, a population group, a trait population (e.g., a group of individuals exhibiting a trait of interest such as a medical condition or response to a therapeutic treatment i.e. drug). Population groups include a group of individuals sharing a common ethno-geographic origin. Reference populations include a group of subjects or individuals who are predicted to be representative of the genetic variation found in the general population. Preferably, the reference population represents the genetic variation in the population at a certainty level of at least 85%, preferably at least 90%, more preferably at least 95% and even more preferably at least 99%.

Frequency data for such alpha-2BAR genotypes or haplotypes in reference and trait populations are useful for identifying an association between a trait and an alpha-2BAR polymorphism, an alpha-2BAR genotype or an alpha-2BAR haplotype. The trait may be any detectable phenotype, including but not limited to genetic predisposition to a disease or response to a treatment, such as for example, agonist or antagonist. These data can be used to determine a measurable or baseline effect of the agonist or antagonist correlated with the polymorphism, genotype or haplotype.

In one embodiment, the method of the present invention includes obtaining data on the frequency of the alpha-2BAR polymorphism, alpha-2BAR genotype or alpha-2BAR haplotype of interest in a reference population as well as in a population exhibiting the trait. Frequency data for one or both of the reference and trait populations may be obtained by genotyping or haplotyping each individual in the populations using one of the methods described herein. In another embodiment, the frequency data for the reference and/or trait populations is obtained by accessing previously determined frequency data, which may be in written or electronic form. For example, the frequency data may be present in a database that is accessible by a computer. Once the frequency data is obtained, the frequencies of the alpha-2BAR polymorphism, alpha-2BAR or alpha-2BAR haplotype of interest are compared in the reference and trait populations. If a alpha-2BAR polymorphism, alpha-2BAR genotype or alpha-2BAR haplotype is more frequent in the trait population than in the reference population to a statistically significant degree, then the trait is predicted to be associated with that alpha-2BAR polymorphism, alpha-2BAR genotype or alpha-2BAR haplotype.

Predicting Individual's Response and Selecting Appropriate Drugs

In a preferred embodiment of the method of the present invention, the trait of interest is a response exhibited by an individual to some therapeutic treatment, for example, response to a drug targeting alpha-2BAR or response to a therapeutic treatment for a disease. As used herein the term "response" means any or all of the following: a quantitative measure of the response, no response, and adverse response (i.e., side effects).

In order to deduce a correlation between a response to a treatment and an alpha-2BAR, alpha-2BAR genotype or alpha-2BAR haplotype, the clinician can obtain data on the clinical responses exhibited by a population of individuals who received the treatment, hereinafter the "clinical population". This clinical data may be obtained by analyzing the results of a clinical trial that has already been run and/or the clinical data may be obtained by designing and carrying out one or more new clinical trials. As used herein, the term "clinical trial" means any research study designed to collect clinical data on responses to a particular treatment, and includes but is not limited to phase I, phase II and phase III clinical trials. Standard methods are used to define the patient population and to enroll subjects.

It is preferred that the individuals included in the clinical population have been assessed for the clinical characteristics of the disease of interest. Such clinical characteristics may include symptoms, disease severity, response to therapy and the like. Characterization of potential patients could employ a standard physical exam or one or more lab tests.

The therapeutic treatment (i.e. drug) of interest is administered to each individual in the trial population and each individual's response to the treatment is measured using one or more predetermined criteria. It is contemplated that in many cases, the trial population will exhibit a range of responses and that the investigator will choose the number of responder groups (e.g., none, low, medium, high) made up by the various responses. In addition, the alpha-2BAR gene for each individual in the trial population is genotyped at least one polymorphic site occurring in the alpha-2BAR, which may be done before or after administering the treatment. As used herein, treatment includes a stimulus (i.e., drug) administered internally or externally to an individual.

After both the clinical and polymorphism data have been obtained, correlations are created between individual response and the presence of the alpha-2BAR polymorphism, alpha-2BAR genotype or alpha-2BAR haplotype. Correlations may be produced in several ways. In one embodiment, individuals are grouped by their alpha-2BAR genotype or alpha-2BAR haplotype and then the averages and standard deviations of responses exhibited by the member of each group are calculated. These results are then analyzed to determine if any observed variation in clinical response between genotype or haplotype groups is statistically significant. Another method involves categorizing the response (e.g., none, low, medium, high or other such grades) and then assessing whether a particular genotype is more common in one group of responders compared to another. Statistical analysis methods which may be used are described in L. D. Fisher and G. vanBelle, "Biostatistics: A Methodology for the Health Sciences", Wiley-Interscience (New York) 1993.

It is also contemplated that the above methods for identifying associations between an alpha-2BAR polymorphism, or alpha-2BAR genotypes and haplotypes having the alpha-2BAR polymorphism, may be performed alone, or in combination with genotype(s) and haplotype(s) for one or more additional genomic regions.

In the most preferred embodiment, the polymorphisms and molecules of the present invention can be used to predict an individual's sensitivity or responsiveness to a pharmaceutical composition or drug, such as for example, an agonists or antagonists. Preferably, the individual's response to an agonist or antagonist, includes detecting a polymorphic site in the polynucleotide encoding the alpha-2B adrenergic receptor molecule comprising SEQ ID NOs: 1 or 2 or fragment or complement thereof; and correlating the polymorphism to a predetermined response for that particular polymorphism, haplotype or genotype, thereby predicting the individual's response to the agonist or antagonist. Accordingly, the present invention can be employed to guide the clinician in the selection of appropriate drug(s) or pharmaceutical composition(s). For example, individuals with a polymorphism comprising DEL301–303 of SEQ ID NO: 2 in the alpha-2BAR molecule are more sensitive to antagonists since endogenous agonist activation of the receptor by catecholamines is increased. Accordingly, with regards to agonists, the response or sensitivity can be predicted to be less for those individuals with the DEL301–303 polymorphism of the alpha-2BAR due to impaired coupling. Using this phenotype, the clinician can administer a higher dose of the agonist to the individual or a different drug altogether.

Alpha-2B adrenergic receptor molecule function or activity can be measured by methods known in the art. Some examples of such measurement include radio-ligand binding to the alpha-2B adrenergic receptor molecule by an agonist or antagonist, receptor-G protein binding, stimulation or inhibition of adenyly cyclase, MAP kinase, phosphorylation or inositol phosphate (IP3).

Figure 3:
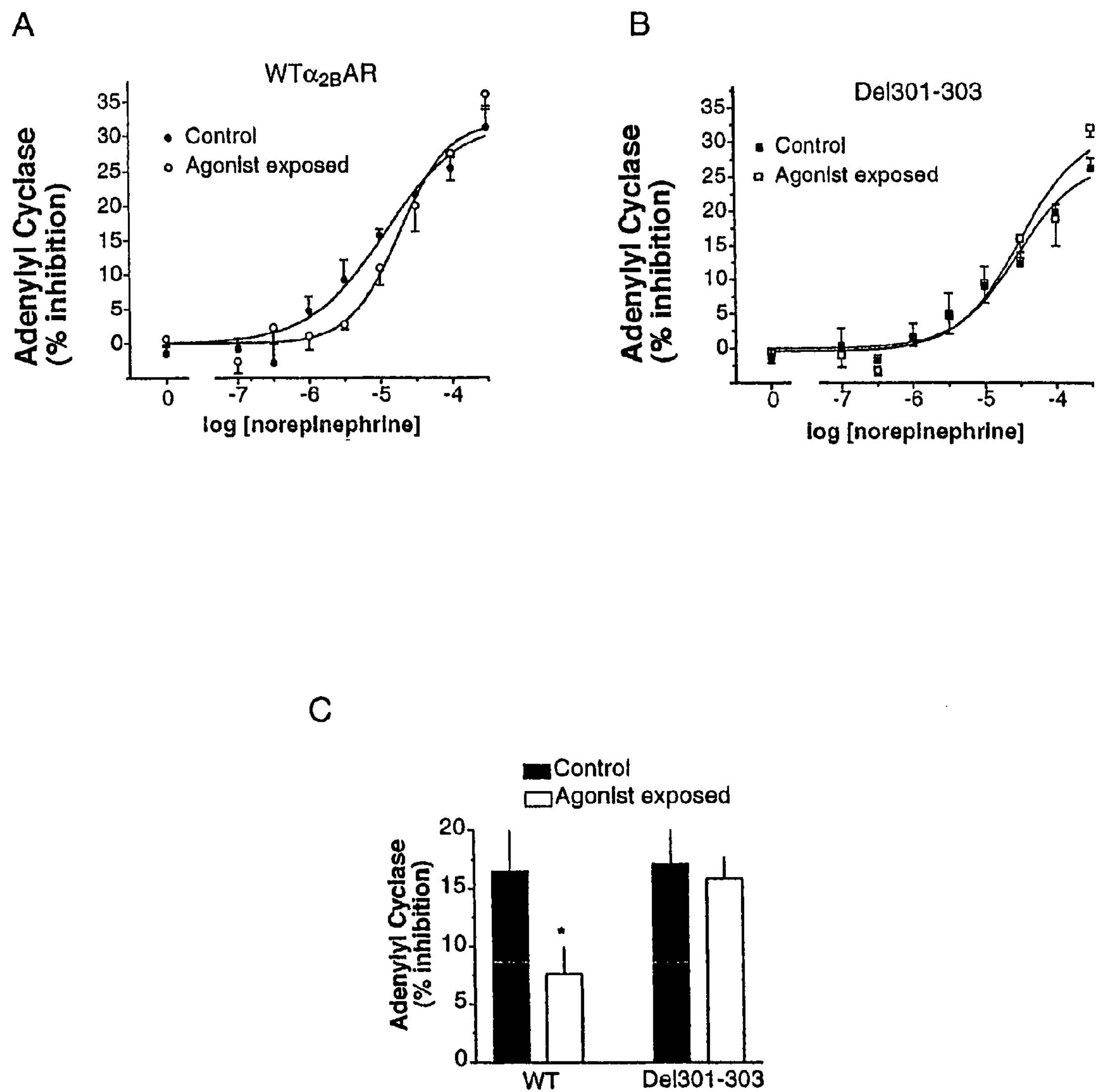
FIG. 3 graphically illustrates that the alpha-2BAR with deletion in amino acids 301 to 303 (Del301–303) of SEQ ID NO: 8, fails to undergo short-term agonist-promoted desensitization. Cells in culture expressing the two receptors were exposed to vehicle or 10 μM norepinephrine for 30 minutes at 37°, washed extensively, membranes prepared and adenylyl cyclase activities determined as described in the examples. Panels A and B show results of full dose-response studies, which reveal that while the wild-type receptor (SEQ ID NO: 7) undergoes desensitization manifested as a rightward shift in the curve, the Del301–303 mutant does not. Panel C shows the percent inhibition of adenylyl cyclase at a submaximal concentration of norepinephrine in the assay (the $EC_{50}$ of the control membranes) for both wild-type and mutant conditions, indicating an ~54% desensitization of wild-type alpha-2BAR. The Del301–303 failed to display such desensitization. Results are from four independent experiments. See also Table 3. *=$p<0.05$ compared to control.

In one embodiment of the present invention, an alpha-2B adrenergic receptor agonist is administered, the agonist activates the alpha-2BAR molecule and $G_i$ coupling results in inhibiting adenylyl cyclase, and decreased phosphorylation. In this embodiment, the mutant alpha-2BAR shows decreased inhibition of adenylyl cyclase (FIGS. 3A–C) as compared to the wild-type alpha-2BAR with insertion of three glutamic acids (IN301–303) at amino acid position 301 to 303 of SEQ ID NO: 7. Thus, mutant alpha-2BAR has decreased receptor activity or function. Preferably, receptor activity is measured by increased or decreased adenyly cyclase, MAP kinase, G protein receptor interaction, inositol phosphate and/or phosphorylation. Increased or decreased adenyly cyclase, MAP kinase, phosphorylation and/or inositol phosphate includes increases or decreases of preferably from about 10% to about 200%, more preferably, from about 20% to about 100%, and most preferably, from about 30% to about 60% from normal levels.

In another embodiment of the present invention, the mutant alpha-2BAR (DEL301–303) showed depressed phosphorylation resulting in loss of short-term agonist-promoted receptor desensitization. Thus, one phenotype of the alpha-2BAR Del301–303 polymorphism is decreased agonist-promoted phosphorylation that results in a complete loss of the ability for the receptor to undergo agonist-promoted desensitization. As used herein, desensitization includes a decline in response resulting from continuous application of agonist or to repeated application or doses. Clinically, desensitization is exhibited by tachyphylaxis. As used herein, tachyphylaxis includes rapidly decreasing response to a drug (i.e. agonist or antagonist) or pharmaceutical composition after administration of more than one dose.

For purposes of the present invention, an agonist is any molecule that activates a receptor. Preferably, the receptor is an alpha-2BAR. Preferred agonists include alpha-2B adrenergic receptor agonists, such as for example, epinephrine, norepinepluine, clonidine, oxymetazoline, guanabenz, UK14304, BHT933 and combinations thereof.

An antagonist is any molecule that blocks a receptor. Preferably, the receptor is an alpha-2BAR. Preferred antagonist include alpha-2B adrenergic receptor antagonists such as for example, yohimbine, prazosin, ARC 239, rauwolscine, idazoxan, tolazoline, phentolamine and combinations thereof.

As used herein a "predetermined response" includes a measurable or baseline effect of the agonist or antagonist correlated with the polymorphism. For example, individuals with the polymorphism wild-type insertion of amino acids 301–303 of the alpha-2B adrenergic receptor molecule display increased alpha agonist promoted coupling to $G_i$ and thus increased inhibition of adenylyl cyclase compared to the polymorphic or mutant alpha-2BAR. Also, the wild-type alpha-2BAR showed increased phosphorylation resulting in gain of short-term agonist-promoted receptor desensitization when compared to the mutant alpha-2BAR. It will be understood by those skilled in the art that other baseline (non-adenylyl cyclase) secondary messenger molecules can be used and correlated to the polymorphism, such as MAP kinase and inositol phosphate.

The present invention includes methods for selecting an appropriate drug or pharmaceutical composition to administer to an individual having a disease associated with alpha-2B adrenergic receptor molecule. The method includes detecting a polymorphic site(s) in the polynucleotide encoding the alpha-2B adrenergic receptor molecule comprising SEQ ID NO: 1 or 2 or fragment or complement thereof in the individual and selecting the appropriate drug based on the polymorphsim or polymorphic site(s) present. The appropriate drug or pharmaceutical composition can be determined by those skilled in the art based on the particular polymorphism identified. For example, individuals with the DEL301–303 polymorphism showed depressed phosphorylation resulting in loss of short-term agonist-promoted receptor desensitization in the alpha-2BAR molecule. Thus, an agonist or antagonist prone to clinical tachyphylaxis can be used in patients with the DEL301–303 polymorphism. However, the response can be decreased due to the altered coupling of alpha-2BAR receptor such that if this were undesirable, another alpha-2BAR agonist can be selected, or another drug in a different class, can be employed. Accordingly, with regards to alpha agonists, the response or sensitivity can be predicted to be less for those individuals with the DEL301–303 polymorphism of the alpha-2BAR. This would lead the clinician to "customize" the choice of agonist based on this polymorphism. The skilled artisan will recognize that individuals with the DEL301–303 would be more sensitive to antagonists by virtue of their receptors being partially dysfunctional due to the polymorphism. Thus, the clinician can "customize" the choice of antagonist based on this polymorphism.

The present invention also contemplates adjusting or changing the dosing regimen of the drug or pharmaceutical composition based on the insertion or deletion present at amino acid positions 301 to 303. For example, individuals with DEL301–303 genotype do not undergo desensitization or tachylphylaxis with the administration of repeated doses over time. Thus, the clinician would not expect the pharmacologic effect of the drug to wane over time. An accelerated dosing regimen could be used in the individual with the DEL301–303 polymorphism without the need for slowly increasing the dose, as would be required in those with the wild-type receptor (IN301–303). Accordingly, individuals with the wild-type genotype (IN301–303) undergo desensitization or tachylphylaxis with the administration of repeated doses over time. Thus, the clinician would expect the pharmacologic effect of the drug to wane over time and the clinician would need to slowly increase the dose over time.

As used herein, "appropriate pharmaceutical composition" includes at least one drug that increases therapeutic efficacy of the drug based on a patient population with a particular disease. Each population will typically have a unique characteristic response to the drug. Knowledge of the efficacies of two or more drugs in treating individuals with different genetic variations provides the opportunity to select the drug effective in treating a large percentage of the total population of individuals while maintaining little or no toxicity.

For the purposes of the present invention, "correlating the polymorphism with a predetermine response" includes associating the predetermined response with the polymorphism that occurs at a higher allelic frequency or rate in individuals with the polymorphism than without. Correlation of the polymorphism with the response can be accomplished by bio-statistical methods known in the art, such as for example, Chi-squared tests or other methods described in L. D. Fisher and G. vanBelle, *Biostatistics: A Methodology for the Health Sciences*, Wiley-Interscience (New York) 1993.

For example, DEL301–303 polymorphism is more common in Caucasians than African-Americans, with allele frequencies of 0.31 and 0.12, respectively. The polymorphism results in depressed phosphorylation causing a loss of short-term agonist-promoted receptor desensitization in the alpha-2BAR molecule. Therefore, an appropriate drug can be selected based upon the individual's pharmaco-ethnogenetics.

For the purposes of the present specification, drugs and pharmaceutical compositions are used interchangeably. Drugs or pharmaceutical compositions contemplated by the present invention include therapeutic compounds such as an analgesic drug, an anesthetic agent, an anorectic agent, an anti-anemia agent, an anti-asthma agent, an anti-diabetic agent, an antihistamine, an anti-inflammatory drug, an antibiotic drug, an antimuscarinic drug, an anti-neoplastic drug, an antiviral drug, a cardiovascular drug, a central nervous system stimulant, a central nervous system depressant, an anti-depressant, an anti-epileptic, an anxyolitic agent, a hypnotic agent, a sedative, an anti-psychotic drug, a beta blocker, a hemostatic agent, a hormone, a vasodilator and a vasoconstrictor. Preferred drugs include the alpha agonists and alpha antagonists. Most preferred drugs include the alpha-2B agonists and alpha-2B antagonists. According to the invention, pharmaceutical compositions or drugs comprising one or more of the therapeutic compounds described above, and a pharmaceutically acceptable carrier or excipient, may be administered to an individual predisposed or having the disease as described, orally, rectally, parenterally, intrasystemically, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions used in the methods of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions used in the present methods may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drugs, it is desirable to slow the absorption from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compounds are mixed with at least one item pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hardfilled gelatin capsules using such excipients as lactose or milk sugar as well as high molecular weight polyethylene glycols and the like.

The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In nonpressurized powder compositions, the active ingredients in finely divided form may be used in admixture with a larger-sized pharmaceutically acceptable inert carrier comprising particles having a size, for example, of up to 100 μm in diameter. Suitable inert carriers include sugars such as lactose. Desirably, at least 95% by weight of the particles of the active ingredient have an effective particle size in the range of 0.01 to 10 μm.

Alternatively, the composition or drugs may be pressurized and contain a compressed gas, such as nitrogen or a liquefied gas propellant. The liquefied propellant medium and indeed the total composition is preferably such that the active ingredients do not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

A further form of topical administration is to the eye. The active compounds are delivered in a pharmaceutically acceptable ophthalmic vehicle, such that the compounds are maintained in contact with the ocular surface for a sufficient time period to allow the compounds to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material.

Compositions for rectal or vaginal administration are preferably suppositories which can be prepared by mixing the active compounds with suitable non-irritating excipients or carriers such as cocoa butter, polyethylene glycol or a suppository wax which are solid at room temperature but liquid at body temperature and therefore melt in the rectum or vaginal cavity and release the drugs.

The compositions used in the methods of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form, in addition to one or more of the active compounds described above, can contain stabilizers, preservatives, excipients and the like. The preferred lipids are the phospholipids and the phosphatidyl cholines (lecithins), both natural and synthetic.

Typical dosages and durations of treatment are as described in clinician's textbooks such as Physician's Desk Reference 2000, incorporated herein by reference, and will be familiar to physicians and other practitioners in the art.

The above methods of the present invention can be used in vivo, in vitro, and ex vivo, for example, in living mammals as well as in cultured tissue, organ or cellular systems. Mammals include, for example, humans, as well as pet animals such as dogs and cats, laboratory animals, such as rats and mice, hamsters and farm animals, such as horses and cows. Tissues, as used herein, are an aggregation of similarly specialized cells which together perform certain special functions. Cultured cellular systems include any cells that express the alpha-2BAR molecule, such as pre and post synaptic neurons in the brain or any cell transfected with the alpha-2B gene.

Having now generally described the invention, the same may be more readily understood through the following reference to the following examples, which are provided by way of illustration and are not intended to limit the present invention unless specified.

EXAMPLES

The examples below describe a polymorphic variant of the human alpha-2BAR which includes a deletion of three glutamic acids (residues 301–303) in the third intracellular loop. This polymorphism was found to be common in Caucasians (31%) and to a lesser extent in African-Americans (12%). The consequences of this deletion were assessed by expressing wild-type and the Del301–303 receptors in CHO and COS cells. Ligand binding was not affected while a small decrease in coupling to the inhibition of adenylyl cyclase was observed with the mutant. The deletion occurs within a stretch of residues which is thought to establish the milieu for agonist-promoted phosphorylation and desensitization of the receptor by G-protein coupled receptor kinases (GRKs). Agonist-promoted phosphorylation studies carried out in cells co-expressing the alpha-2BARs and GRK2 revealed that the Del301–303 receptor displayed ~56% of wild-type phosphorylation. Furthermore, the depressed phosphorylation imposed by the deletion was found to result in a complete loss of short-term agonist-promoted receptor desensitization. Thus the major phenotype of the Del301–303 alpha-2BAR is one of impaired phosphorylation and desensitization by GRKs, and thus the polymorphisms renders the receptor incapable of modulation by a key mechanism of dynamic regulation.

Example 1

Polymorphism Detection

The nucleic acid sequence encoding the third intracellular loop of the human alpha-2BAR (GenBank accession # AF005900, SEQ ID NO:1) was examined for polymorphic variation by performing polymerase chain reactions (PCR) to amplify this portion of the cDNA from genomic DNA derived from blood samples. In this application the adenine of the initiator ATG codon of the open reading frame of the receptor is designated as nucleotide 1 and amino acid 1 is the encoded methionine. The human receptor consists of 450 amino acids. For initial examination, DNA from 39 normal individuals was utilized. Two overlapping fragments encompassing the third intracellular loop region were generated using the following primers pairs: fragment 1 (534 bp), 5'-GCTCATCATCCCTTTCTCGCT-3' (sense) SEQ ID NO: 13 and 5'-AAAGCCCCACCATGGTCGGGT-3' (antisense) SEQ ID NO; 14 and fragment 2 (588 bp), 5'-CTGATCGCCAAACGAGCAAC-3' (sense) SEQ ID NO: 15 and 5'-AAAAACGCCAATGACCACAG-3' SEQ ID NO: 16 (antisense). The 5' end of each sense and antisense primer also contained sequences corresponding to the M13 forward (5'-TGTAAAACGACGGCCAGT-3') SEQ ID NO: 17 and M13 reverse (5'-CAGGAAACAGCTATGACC-3') SEQ ID NO: 18 universal sequencing primers, respectively. The PCR reactions consisted of ~100 ng genomic DNA, 5 pmol of each primer, 0.8 mM dNTPs, 10% DMSO, 2.5 units Platinum taq™ DNA polymerase (Gibco/RL), 20 μL 5× buffer J (Jnvitrogenn) in a 100 μl reaction volume. Reactions were started by an initial incubation at 94° C. for four minutes, followed by 35 cycles of 94° C. for 30 seconds, 58° C. (fragment 1) or 60° C. (fragment 2) for 30 seconds, and 72° C. for one minute, followed by a final extension at 72° C. for seven minutes. PCR reactions were purified using the QIAquick™ PCR purification system (Qiagen), and automated sequencing of both strands of each PCR product was performed using Applied Biosystems 370 sequencer using dye primer methods. As discussed, a 9 bp in frame deletion at nucleotide positions 901 to 909 occurring in SEQ ID NO: 2 was detected which resulted in a loss of three glutamic acid residues at amino acid positions 301–303. Thus, this polymorphism was denoted Del301–303. Of note, previous reports have identified this polymorphism (Heinonen, P., Koulu, M., Pesonen, U., Karvonen, M. K., Rissanen, A., Laakso, M., Valve, R., Uusitupa, M., and Scheinin, M. (1999) *J Clin Endocrinol Metab* 84, 2429–2433; Baldwin, C. T., Schwartz, F., Balms, 7., Burzstyn, M., DeStefano, A. L., Gavras, L., Handy, D. E., Joost, O., Martel, T., Manolis, A., Nicolaou, M., Bresnahan, M., Farrer, L., and Gavras, H. (1999) *Am J Hypertens* 12, 853–857). Heinonen et al. refer to the polymorphism as Del 297–299 or DEL 298–300 (which may be a numbering error) while Baldwin et al. refer to it as a 9-base in-frame deletion corresponding loss of 3 glutamic acid residues. No other nonsynonymous or synonymous polymorphisms were identified. PCR amplification of 209 and 200 bp fragments encompassing this polymorphic region allowed screening of additional DNA samples whose genotypes were distinguished by size when run on 4% Nuseive agarose gels. PCR conditions were the same as described above except that buffer F was used with the following primers: 5'-AGAAGGAGGGTGTTTGTGGGG-3' (sense) SEQ ID NO: 19 and 5'-ACCTATAGCACCCACGCCCCT-3' (antisense) SEQ ID NO: 20.

Example 2

Constructs and Cell Transfection

To create the polymorphic alpha-2BAR construct, a 1585 bp PCR product encompassing the alpha-2BAR gene was amplified from a homozygous deletion individual using the following primers: 5'-GGCCGACGCTCTTGTCTAGCC-3' (SEQ ID NO: 21) and 5'-CAAGGGGTTCCTAAGATGAG-3' (SEQ ID NO: 22). This fragment was digested and subcloned into the Xcm I and BamH I sites of the wild-type alpha-2BAR sequence in the expression vector pBC12BI (Eason, M. G. and Liggett, S. B. (1992) *J. Biol. Chem.* 267, 25473–25479). The integrity of the construct was verified by sequencing. Chinese hamster ovary cells (CHO-K1) were stably transfected by a calcium phosphate precipitation technique as previously described using 30 µg of each receptor construct and 0.5 µg of $pSV_2neo$ to provide for G418 resistance (Eason, M. G., Jacinto, M. T., and Liggett, S. B. (1994) *Mol. Pharmacol.* 45, 696–702). Selection of positive clones was carried out in 1.0 mg/ml G418 and expression of the alpha-2BAR from individual clonal lines was determined by radioligand binding as described below. Several clonal lines with matched expression levels between 500–1000 fmol/mg were utilized as indicated. Cells were grown in monolayers in Ham's F-12 medium supplemented with 10% fetal calf serum, 100 units/ml penicillin, 100 µg/ml streptomycin and 80 µg/ml G418 (to maintain selection pressure) at 37° C. in a 5% $CO_2$ atmosphere. For phosphorylation experiments, receptors were epitope tagged with the influenza hemagglutinin nonopeptide YPYDVPDYA (SEQ ID NO: 23) at the amino terminus. This was accomplished by constructing vectors using the above constructs with insertions of in-frame sequence encoding the peptide using PCRs essentially as previously described (Jewell-Motz, E. A., Small, K. M., and Liggett, S. B. (2000) *J. Biol. Chem.*). Tagged receptors were expressed at ~15 pmol/mg, along with GRK2 (βARK1), in COS-7 cells using a DEAE Dextran technique as described (Eason, M. G., Moreira, S. P., and Liggett, S. B. (1995) J. Biol. Chem. 270, 4681–4688).

Example 3

Adenylyl Cyclase Activities

Alpha-2BAR inhibition of adenylyl cyclase was determined in membrane preparations from CHO cells stably expressing the two receptors using methods similar to those previously described (Small, K. M., Forbes, S. L., Rahman, F. F., Bridges, K. M., and Liggett, S. B. (2000) J. Biol. Chem. 275, 23059–23064). Briefly, cell membranes (~20 µg) were incubated with 27 µM phosphoenolpyruvate, 0.6 µM GTP, 0.1 mM cAMP, 0.12 mM ATP, 50 µg/ml myokinase, 0.05 mM ascorbic acid and 2 µCi of [α-32P]ATP in a buffer containing 40 mM HEPES, pH 7.4, 1.6 mM MgCl2 and 0.8 mM EDTA for 30 minutes at 37° C. Activities were measured in the presence of water (basal), 5 µM forskolin, and 5 µM forskolin with the indicated concentrations of agonists. Reactions were terminated by the addition of a stop solution containing excess ATP and cAMP and ~100,000 dpm of [3H]cAMP. Labeled cAMP was isolated by gravity chromatography over alumina columns with [3H]cAMP used to quantitate column recovery. Results are expressed as percent inhibition of forskolin stimulated activity. For desensitization experiments, cells were pretreated for 30 min at 37° with media alone or with media containing 10 µM norepinephrine, placed on ice, and washed five times with cold PBS prior to membrane preparation. Desensitization of alpha-2BAR is manifested by a shift to the right in the dose-response curve for the inhibition of adenylyl cyclase (i.e., increase in EC50) without a significant change in the maximal response (Eason, M. G. and Liggett, S. B. (1992) *J. Biol. Chem.* 267, 25473–25479; Jewell-Motz, E. A. and Liggett, S. B. (1995) Biochem 34, 11946–11953; Kurose, H. and Lefkowitz, R. J. (1994) J. Biol. Chem. 269, 10093–10099). To quantitate the magnitude of this desensitization, the inhibitory response under control conditions at a submaximal concentration of agonist (the EC50) in the assay was determined from the curve and compared to the response to this same concentration from membranes derived from cells exposed to norepinephrine. This method has been previously validated (Kurose, H. and Lefkowitz, R. J. (1994) J. Biol. Chem. 269, 10093–10099) in several G protein coupled receptor systems.

Example 4

Radioligand Binding

Expression of mutant and wild-type alpha-2BAR was determined using saturation binding assays as described (Small, K. M., Forbes, S. L., Rahman, F. F., Bridges, K. M., and Liggett, S. B. (2000) *J. Biol. Chem.* 275, 23059–23064; Hausdorff, W. P., Bouvier, M., O'Dowd, B. F., Irons, G. P., Caron, M. G., and Lefkowitz, R. J. (1989) *J. Biol. Chem.* 264, 12657–12665; Baron, B. M. and Siegel, B. W. (1990) *Mol Pharmacol* 38, 348–356) with [$^3$H]yohimbine or [$^{125}$I] aminoclonidine with 10 µM phentolamine or 10 µM yohimbine, respectively, used to define nonspecific binding. For competition studies, membranes were incubated in 50 mM Tris-HCL, pH 7.4, 10 mM $MgSO_4$, 0.5 mM EDTA with 2.0 nM [$^3$H]yohimbine and 16 concentrations of the indicated competitor in the absence or presence of guanine nucleotide for 30 minutes at 25° C. Reactions for the above radioligand binding studies were terminated by dilution with 4 volumes of ice cold 10 mM Tris-HCL, pH 7.4 buffer and vacuum filtration over Whatmann GF/C glass fiber filters.

Example 5

Intact Cell Receptor Phosphorylation

Transiently transfected COS-7 cells expressing equivalent levels of each receptor were grown to confluence and incubated with [$^{32}$P] orthophosphate (~4 mCi/100 mm plate) for 2 h at 37° C. in 5% $CO_2$ atmosphere. Cells were then incubated in the presence or absence of 100 µM norepinephrine for 15 min, washed 5 times with ice-cold PBS, solubilized in 1 ml of a buffer containing 1% Triton-X 100, 0.05% SDS, 1 mM EDTA, and 1 mM EGTA in PBS, by rotation in a microcentrifuge tube for 2 h at 4° C. This and all subsequent steps included the protease inhibitors benzamidine (10 µg/ml), soybean trypsin inhibitor (10 µg/ml), aprotinin (10 mg/ml), and leupeptin (5 µg/ml) and the phosphatase inhibitors sodium fluoride (10 mM) and sodium pyrophosphate (10 mM). (A separate flask was scraped in 5 mM Tris/2 mM EDTA and membranes prepared for radioligand binding as described above.) Unsolubilized material was removed by centrifugation at 40000 g at 4° C. for 10 min. The HA epitope tagged alpha-2BARs were immunoprecipitated using an anti-HA high affinity monoclonal antibody (Roche) as previously described (Jewell-Motz, E. A., Small, K. M., and Liggett, S. B. (2000) *J. Biol. Chem.*). Briefly, solubilized material was preincubated for 2 h at 4° C. with protein G Sepharose beads to remove nonspecific binding. The supernatant was then incubated with protein G Sepharose beads and a 1:200 dilution of antibody for 18 h at 4° C. Following immunoprecipitation, the beads were washed 3 times by centrifugation and resuspension, and then incubated at 37° C. for 1 hour in SDS sample buffer. Proteins in the supernatant were then fractionated on a 10% SDS-polyacrylamide gel with equal amounts of receptor (based on radioligand binding) loaded in each lane. Signals were visualized and quantitated using a Molecular Dynamics PhosphorImager with ImageQuant™ Software.

Example 6

Protein Determination, Adenylyl Cyclase and Radioligand Binding Assay and Genotype Protein determinations were by the copper bicinchoninic acid method (Smith, P. K., Krohn, R. I., Hermanson, G. T., Mallia, A. K., Gartner, F. H., Provenzano, M. D., Fujimoto, E. K., Goeke, N. M., Olson, B. J., and Klenk, D.C. (1985) *Anal. Biochem.* 150, 76–85). Data from adenylyl cyclase and radioligand binding assays were analyzed by iterative least-square techniques using Prizm™ software (GraphPad, San Diego, Calif.). Agreement between genotypes observed and those predicted by the Hardy-Weinberg equilibrium was assessed by a Chi-squared test with one degree of freedom. Genotype comparisons were by Fisher's exact test. Comparisons of results from biochemical studies were by t-tests and significance was considered when $p<0.05$. Data are provided as means ± standard errors.

Results and Discussion of Examples 1–6

Sequence analysis of the third intracellular loop of the alpha-2BAR gene from 78 chromosomes revealed a single sequence variant. This consisted of an in-frame 9 bp deletion (GAAGAGGAG, SEQ ID NO: 3) beginning at nucleotide 901 of SEQ ID NO: 1 (FIG. 1*a*) that results in loss of three glutamic acid residues at amino acid positions 301–303 (SEQ ID NO:11) of the third intracellular loop of the receptor (FIG. 2). Using the rapid detection method (FIG. 1*b*), allele frequencies were determined in a larger population of apparently normal Caucasians and African-Americans. The frequencies of the wild-type and the Del301–303 (mutant) polymorphic alpha-2BAR are shown in Table 1.

The deletion polymorphism is more common in Caucasians than African-Americans, with allele frequencies of 0.31 and 0.12, respectively. The distribution of homozygous and heterozygous alleles in either population was not different than that predicted from the Hardy-Weinberg equilibrium ($p>0.8$).

The consequences of this polymorphism on ligand binding and receptor function were evaluated by stably expressing the human wild-type alpha-2BAR and the Del301–303 receptor in CHO cells (shown in Table 2)

Saturation radioligand binding studies revealed a small but statistically significant lower affinity for the alpha-2BAR antagonist [$^3$H]yohimbine for Del301–303 compared to the wild-type receptor ($K_d$=5.1±0.2 vs 3.8±0.3 nM, respectively, n=5, $p<0.05$). Agonist (epinephrine) competition binding experiments carried out in the presence of GppNHp revealed a small increase in the $K_i$ for the polymorphic receptor (285±8.7 vs 376±66 nM, n=5, $p<0.05$). In similar studies carried out in the absence of guanine nucleotide, two-site fits were obtained for both receptors with no differences in the $K_L$ or the percentage of receptors in the high affinity state (% $R_H$, Table 2). However, a trend towards an increased $K_H$ was observed with the Del301–303 mutant. These results prompted additional studies with the partial agonist radioligand [$^{125}$I]-aminoclonidine. Saturation binding studies (in the absence of GppNHp) with concentrations of the ligand from 0.2–4 nM revealed a single site with a $K_d$~1 nM as reported by others (Baron, B. M. and Siegel, B. W. (1990) *Mol Pharmacol* 38, 348–356). Comparison of the wild-type alpha-2BAR and the Del301–303 receptor revealed essentially identical $K_d$s for [$^{125}$I]-aminoclonidine (1.33±0.12 vs 1.22±0.07 nM, respectively). Taken together, the data suggest that there is little, if any, effect of the deletion in the third intracellular loop on the conformation of the ligand binding pocket within the transmembrane spanning domains.

To address the functional consequences of the mutation, studies examining agonist-promoted inhibition of forskolin stimulated adenylyl cyclase activities were carried out in lines expressing the wild-type alpha-2BAR and the Del301–303 receptor at densities of 626±54 and 520±82 fmol/mg (n=7, $p>0.05$). The results of these studies are shown in Table 3.

As can be seen, the Del301–303 receptor displayed less inhibition of adenylyl cyclase (23.4±2.2%) compared to wild-type alph-2BAR (28.5±1.6%, $p<0.05$). Furthermore, the polymorphic receptor had a greater $EC_{50}$ (19.6±5.5 vs 7.9±2.1 nM, $p<0.01$). Thus, the loss of the three glutamic acids in the third intracellular loop, which is known to contain regions important for G-protein coupling, results in a modest decrease in agonist-mediated receptor function.

The deletion polymorphism occurs in a highly acidic stretch of amino acids (EDEAEEEEEEEEEEEE, SEQ ID NO: 9) within the third intracellular loop of alpha-2BAR (FIG. 2). The structural importance of this region has been previously assessed and shown to be critical for short-term agonist-promoted receptor phosphorylation leading to desensitization (Jewell-Motz, E. A. and Liggett, S. B. (1995) *Biochem* 34, 11946–11953). These data and reports by others (Onorato, J. J., Palczewski, K., Regan, J. W., Caron, M. G., Lefkowitz, R. J., and Benovic, J. L. (1991) *Biochem* 30, 5118–5125) suggest that this acidic environment is necessary for receptor phosphorylation by GRKs. Therefore, to investigate the consequences of this deletion polymorphism on receptor desensitization, agonist-promoted inhibition of adenylyl cyclase activity was determined in membranes from CHO cells expressing the wild-type and Del301–303 receptor after pretreatment with norepinephrine. In these experiments, cells were incubated with media alone or media containing agonist (10 μM norepinephrine) for 30 min and extensively washed, membranes prepared, and agonist-mediated inhibition of forskolin stimulated adenylyl cyclase activity was determined. As described previously (Eason, M. G. and Liggett, S. B. (1992) *J. Biol. Chem.* 267, 25473–25479) and shown in FIG. 3 and Table 3, desensitization of wild-type alpha-2BAR expressed in CHO cells is manifested by an increase in the $EC_{50}$ for agonist-mediated inhibition of adenylyl cyclase. Analysis of composite curves derived from four independent experiments shows an increase from 7.4 μM to 29.4 μM for the wild-type alpha-2BAR. In contrast, there was no change in the $EC_{50}$ for the deletion receptor following agonist pretreatment (29.5 μM versus 31.2 μM). Desensitization was quantitated by examining adenylyl cyclase activities at a submaximal concentration of agonist (the $EC_{50}$ for the control condition). At this concentration, wild-type alpha-2BAR inhibited adenylyl cyclase activity by 16.5±3.9%; with agonist preexposure, inhibition at this same concentration of agonist was 7.6±2.3%, (n=4, p<0.05, FIG. 3c), amounting to 54% desensitization of receptor function. Submaximal inhibition of adenylyl cyclase for the Del301–303 receptor, however, was not different between control and agonist-treated cells (17.1±3.0% vs 15.9±1.7%, n=4, p=ns). In another two cell lines with matched expression of ~600 fmol/mg, the same desensitization phenotypes for wild-type and the Del301–303 polymorphic receptor were observed (data not shown).

Figure 4:
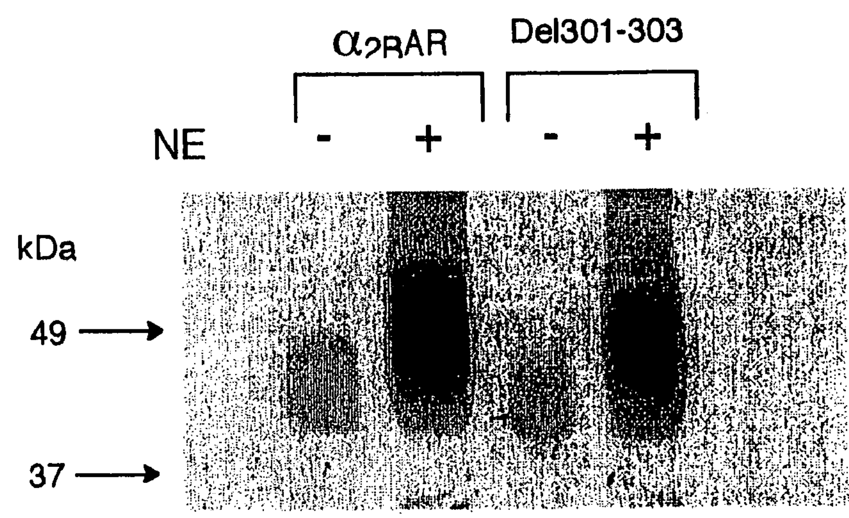
FIG. 4 illustrates that alpha-2BAR with deletion in amino acids 301 to 303 (Del301–303) has impaired agonist-promoted phosphorylation. Cells co-expressing each receptor and GRK2 were incubated with $^{32}$P-orthophosphate, exposed to 10 μM norepinephrine for 15 minutes, and receptor purified by immunoprecipitation as described in the examples. Shown is an autoradiogram from a single experiment representative of four performed.

We next performed whole cell phosphorylation studies of the wild-type and polymorphic alpha-2BAR under the same conditions as those used for desensitization. We hypothesized that agonist-promoted phosphorylation would be decreased in the polymorphic receptor. However, given that this receptor displays rightward-shifted dose response curves for inhibition of adenylyl cyclase at baseline, we also considered the possibility that the receptor is significantly phosphorylated in the basal state. Studies were carried out in cells co-transfected with the receptor and GRK2 (PARK1), a strategy that we have previously shown to be useful in identifying receptor-GRK interactions (Jewell-Motz, E. A. and Liggett, S. B. (1996) *J. Biol. Chem.* 271, 18082–18087). The results of a representative study are shown in FIG. 4*a* and mean results from four experiments in FIG. 4*b*. The wild-type alpha-2BAR underwent a 5.84±0.49 fold increase in phosphorylation with agonist exposure. In contrast, while the Del301–303 receptor displayed some degree of agonist-promoted phosphorylation, the extent was clearly less (3.28±0.24 fold, p<0.05 compared to wild-type). Basal phosphorylation was equivalent between the two receptors.

It is interesting to note that this partial loss of phosphorylation results in a receptor that fails to undergo any degree of functional desensitization. While it might seem reasonable to assume that such phosphorylation would be associated with some degree of desensitization, several previous studies with the $\alpha_{2A}$- and alpha-2BAR subtypes indicate that full (i.e., wild-type) phosphorylation is necessary for the desensitization process (Eason, M. G., Moreira, S. P., and Liggett, S. B. (1995) *J. Biol. Chem.* 270, 4681–4688; Jewell-Motz, E. A. and Liggett, S. B. (1995) *Biochem* 34, 11946–11953; Jewell-Motz, E. A., Small, K. M., and Liggett, S. B. (2000) *J. Biol. Chem.*). For the $\alpha_{2A}$AR, we have shown that four serines in the third intracellular loop are phosphorylated after agonist exposure (Eason, M. G., Moreira, S. P., and Liggett, S. B. (1995) *J. Biol. Chem.* 270, 4681–4688). Removal of serines by alanine substitution mutagenesis results in a proportional decrease in phosphorylation. Such partial phosphorylation (compared to wild-type), however, was found to be insufficient to cause any detectable desensitization. In a previous study of the alpha-2BAR, we deleted the entire aforementioned acidic region (Jewell-Motz, E. A. and Liggett, S. B. (1995) *Biochem* 34, 11946–11953). Agonist-promoted phosphorylation was reduced by 50% in this mutant, and desensitization was ablated. These results are entirely consistent with the current work, where a restricted substitution resulted in a decrease in phosphorylation and a complete loss of desensitization. Finally, we have also recently shown that a chimeric alpha-2A/alpha-2CAR which undergoes agonist-promoted phosphorylation, fails to exhibit desensitization (Jewell-Motz, E. A., Small, K. M., and Liggett, S. B. (2000) *J. Biol. Chem.*). Taken together with our current work, these results indicate that the conformation of the third loop evoked by GRK mediated phosphorylation which provides for the binding of arrestins (which is the ultimate step that imparts uncoupling) is highly specific. Thus a precise phosphorylation-dependent conformation is apparently required for arrestin binding to alpha-2AR and subsequent functional desensitization. Perturbations of the milieu can thus have significant functional consequences, as occurs with the Del301–303 polymorphic alpha-2BAR.

Thus the major signaling phenotypes of the alpha-2BAR Del301–303 polymorphism is one of decreased agonist-promoted phosphorylation which results in a complete loss of the ability for the receptor to undergo agonist-promoted desensitization and a decrease in receptor coupling. The potential physiologic consequences of the polymorphism could be related to either or both of the above phenotypes. A receptor that fails to undergo desensitization would be manifested as static signaling despite continued activation of the receptor by endogenous or exogenous agonist. Such a lack of regulation by agonist may perturb the dynamic relationship between incoming signals and receptor responsiveness that maintains homeostasis under normal or pathologic conditions. Recently, Gavras and colleagues (Makaritsis, K. P., Handy, D. E., Johns, C., Kobilka, B., Gavras, I., and Gavras, H. (1999) *Hypertension* 33, 14–17) have shown that alpha-2B−/+mice fail to display a hypertensive response to salt loading after subtotal nephrectomy. Thus a polymorphic alpha-2BAR that fails to desensitize (i.e., does not display regulatable function) may predispose to salt-sensitive hypertension. Regarding the therapeutic response to alpha-2AR agonists, the phenotype of the Del301–303 receptor indicates that individuals with this polymorphism would display little tachyphylaxis to continued administration of agonists. In addition, the initial response to agonist would also be reduced based on the somewhat depressed coupling of the Del301–303 receptor.

Until recently, it has been difficult to differentiate alpha-2BAR function from the other two subtypes in physiologic studies. With the development of knock-out mice lacking each $\alpha_2$AR subtype (Hein, L., Limbird, L. E., Eglen, R. M., and Kobilka, B. K. (1999) *Ann NY Acad Sci* 881, 265–271; Rohrer, D. K. and Kobilka, B. K. (1998) *Physiol Rev* 78, 35–525, 6, Link, R. E., Desai, K., Hein, L., Stevens, M. E., Chruscinski, A., Bernstein, D., Barsh, G. S., and Kobilka, B. K. (1996) *Science* 273, 803–805; MacMillan, L. B., Hein, L., Smith, M. S., Piascik, M. T., and Limbird, L. E. (1996) *Science* 273, 801–805), certain functions can now be definitively attributed to specific subtypes. Characterization of the alpha-2BAR knock-out mouse has indicated that the alpha-2BAR subtype is expressed on vascular smooth muscle and is responsible for the hypertensive response to $\alpha_2$AR agonists (Link, R. E., Desai, K., Hein, L., Stevens, M. E., Chruscinski, A., Bernstein, D., Barsh, G. S., and Kobilka, B. K. (1996) *Science* 273, 803–805). This indicates that vascular alpha-2BAR contribute to overall vascular tone and thus participate in systemic blood pressure regulation. This role may be more important, though, during adaptive conditions, such as salt loading, since resting blood pressure is normal in the heterozygous alpha-2B −/+ mice (Makaritsis, K. P., Handy, D. E., Johns, C., Kobilka, B., Gavras, I., and Gavras, H. (1999) *Hypertension* 33, 14–17). Whether the alpha-2B −/− mice have altered resting blood pressures has not been studied in detail due to high perinatal lethality of the homozygous knockout (Link, R. E., Desai, K., Hein, L., Stevens, M. E., Chruscinski, A., Bernstein, D., Barsh, G. S., and Kobilka, B. K. (1996) *Science* 273, 803–805). However, neither the region of chromosome 2 near the alpha-2BAR coding sequence, nor the deletion polymorphism, have been linked or associated with hypertension (Heinonen, P., Koulu, M., Pesonen, U., Karvonen, M. K., Rissanen, A., Laakso, M., Valve, R., Uusitupa, M., and Scheinin, M. (1999) *J Clin Endocrinol Metab* 84, 2429–2433; Baldwin, C. T., Schwartz, F., Baima, J., Burzstyn, M., DeStefano, A. L., Gavras, I., Handy, D. E., Joost, O., Martel, T., Manolis, A., Nicolaou, M., Bresnahan, M., Farrer, L., and Gavras, H. (1999) *Am J Hypertens* 12, 853–857; Munroe, P. B. and Caulfield, M. J. (2000) *Curr Opin Genet Dev* 10, 325–329). No studies, though, have assessed whether the polymorphism is associated with salt-sensitive hypertension or other phenotypes, or the response to alpha-2BAR agonist.

In summary, we have delineated the signalling phenotype of a polymorphism of the alpha-2BAR that results in a deletion of three glutamic acids in the third intracellular loop of the receptor. The polymorphism is prevalent in the human population, with a frequency that is ~2 fold greater in Caucasians as compared to African-Americans. The polymorphic receptor displays wild-type agonist binding affinity but a small decrease in function in the resting state. The major phenotype, though, is a significant decrease in agonist-promoted phosphorylation by GRKs, which results in a receptor that fails to display agonist-promoted desensitization. To our knowledge this is the first polymorphism of any G-protein coupled receptor to affect GRK-mediated phosphorylation.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice thin the art to which the invention pertains and as may be applied to the essential features hereinbefore set forth and as follows in the scope of the appended claims.

TABLE 1

Frequency of the Alpha-2BAR Del301–303 polymorphism.

| | n | Wt Homozygous | Hetero-zygous | Del301–303 Homozygous | Del301–303 Allele Frequency |
|---|---|---|---|---|---|
| Caucasian | 94 | 41 | 47 | 6 | 0.31 |
| African-American | 79 | 61 | 17 | 1 | 0.12 |

TABLE 2

Ligand binding properties of wild-type and Del301–303 alpha-2BAR expressed in CHO cells

| | $[^3H]$-yohimbine | | | | | | $[^{125}I]$-aminoclonidine | |
|---|---|---|---|---|---|---|---|---|
| | saturation binding | | epinephrine competition | | | | saturation binding | |
| Receptor | $B_{max}$ (fmol/mg) | $K_D$ (nM) | $K_i$ | $K_H$ (nM) | $K_L$ (nM) | % $R_H$ | $B_{max}$ (fmol/mg) | $K_D$ (nM) |
| Wild-Type | 671 ± 56 | 3.8 ± 0.3 | 285 ± 8.7 | 2.9 ± 0.8 | 346 ± 111 | 41 ± 4 | 118 ± 27 | 1.33 ± 0.12 |
| Del301–303 | 538 ± 79 | 5.1 ± 0.2* | 376 ± 66* | 4.1 ± 1.2 | 357 ± 135 | 42 ± 5 | 106 ± 20 | 1.22 ± .07 |

Saturation binding isotherms and competition studies were carried out with membranes from CHO cells expressing equivalent levels of receptor.
*$p < 0.05$ compared to wild-type alpha-2BAR.

TABLE 3

Adenylyl cyclase activities of the wild-type and Del301–303 alpha-2BAR expressed in CHO cells

| | Basal | Forskolin | Max | | Submax inhibition (%) | | Desensitization |
|---|---|---|---|---|---|---|---|
| | pmol/min/mg | | Inhibition (%) | $EC_{50}$ (nM) | Ctrl | NE | (%) |
| Wild Type | 2.0 ± 0.2 | 15.1 ± 0.9 | 28.5 ± 1.6 | 7.9 ± 2.1 | 16.5 ± 3.9 | 7.6 ± 2.3† | 54 |
| Del301–303 | 1.2 ± 0.1* | 11.9 ± 0.9* | 23.4 ± 2.2* | 19.6 ± 5.5* | 17.1 ± 3.0 | 15.9 ± 1.7* | 7 |

Adenylyl cyclase activities were determined in membranes in response to forskolin (5 μM) and forskolin plus various concentrations of norepinephrine. See also FIG. 3.
*$p < 0.05$ compared to wild-type alpha-2BAR.
†$p < 0.05$ compared to control.

What is claimed is:

1. A method of establishing an alpha-2B-adrenergic receptor function comprising:

a. obtaining an isolated polynucleotide that encodes said alpha-2B-adrenergic receptor, or a complement thereof, or a fragment thereof, or a complement of said fragment, that includes nucleotides 901 to 909 of SEQ ID NO: 1, or nucleotides 901 to 909 of SEQ ID NO: 2, or their complements;

b. detecting in said isolated polynucleotide the presence or absence of a deletion polymorphism, said deletion polymorphism exclusively consisting of the deletion of nucleotide positions 901 to 909 of SEQ ID NO: 1; and c. establishing that the agonist-mediated receptor function of decreasing adenylyl cyclase activity of said alpha-2B-adrenergic receptor is reduced if said deletion polymorphism is present as compared to said agonist-mediated receptor function if said deletion polymorphism is absent.

2. A method according to claim 1, wherein said detecting comprises a hybridization step.

3. A method of phenotyping an individual, comprising:

establishing the alpha-2B-adrenergic receptor function according to claim 1, thereby determining phenotype of said individual from whom said isolated polynucleotide was obtained.

4. The method according to claim 2, further comprising amplifying the deletion polymorphism of the polynucleotide prior to the hybridization.

5. The method according to claim 2, wherein said hybridization is selected from the group consisting of southern blot, dot blot, reverse dot blot, northern blot, and allele-specific oligonucleotide hybridization.

6. The method according to claim 2, wherein the hybridization includes hybridization of an oligonucleotide to a region of the polynucleotide, the oligonucleotide being labeled with a label selected from the group consisting of radiolabel, fluorescent label, bioluminescent label, chemiluminescent label, nucleic acid label, hapten label, and enzyme label.

7. The method according to claim 2, wherein said detecting comprises a step selected from the group consisting of dideoxy sequencing, restriction digestion, allele-specific polymerase reaction, single-stranded conformational polymorphism analysis, genetic bit analysis, temperature gradient gel electrophoresis; ligase chain reaction, or ligase/polymerase genetic bit analysis, and random amplification of DNA.

8. The method according to claim 6, wherein the oligonucleotide is from about 10 to about 50 nucleotides in length.

9. A method of establishing an alpha-2B-adrenergic receptor function comprising:

a. obtaining an isolated polynucleotide that encodes said alpha-2B-adrenergic receptor or a complement thereof, or a fragment thereof, or a complement of said fragment, that includes nucleotides 901 to 909 of SEQ ID NO: 1, or nucleotides 901 to 909 of SEQ ID NO: 2, or their complements;

b. indirectly detecting in said isolated polynucleotide the presence or absence of a deletion polymorphism, said deletion polymorphism exclusively consisting of the deletion of nucleotide positions 901 to 909 of SEQ ID NO: 1; and c. establishing that the agonist-mediated receptor function of decreasing adenylyl cyclase activity of said alpha-2B-adrenergic receptor is reduced if said deletion polymorphism is present as compared to said agonist-mediated receptor function if said deletion polymorphism is absent.

10. The method of claim 1, wherein the agonist is selected from a group consisting of epinephrine, norepinephrine, clonidine, oxymetazoline, guanabenz, UK14304, BHT933 and combinations thereof.

11. The method of claim 9, wherein the agonist is selected from a group consisting of epinephrine, norepinephrine, clonidine, oxymetazoline, guanabenz, UK14304, BHT933 and combinations thereof.

* * * * *